US008287855B2

(12) United States Patent
Killeen et al.

(10) Patent No.: US 8,287,855 B2
(45) Date of Patent: Oct. 16, 2012

(54) *V. CHOLERAE* HYPEREXPRESSING RECOMBINANT CHOLERA TOXIN B SUBUNIT SHOWING DUAL IMMUNOGENICITY

(75) Inventors: Kevin P. Killeen, Milton, MA (US); Kenneth L. Roland, Mesa, AZ (US); Lawrence J. Thomas, South Easton, MA (US)

(73) Assignee: Celldex Therapeutics, Inc., Needham, MA (US)

( * ) Notice: Subject to any disclaimer, the term of this patent is extended or adjusted under 35 U.S.C. 154(b) by 198 days.

(21) Appl. No.: 12/451,101

(22) PCT Filed: Apr. 24, 2008

(86) PCT No.: PCT/US2008/005261
§ 371 (c)(1),
(2), (4) Date: Oct. 23, 2009

(87) PCT Pub. No.: WO2008/133926
PCT Pub. Date: Nov. 6, 2008

(65) Prior Publication Data
US 2010/0129396 A1    May 27, 2010

Related U.S. Application Data

(60) Provisional application No. 60/926,123, filed on Apr. 24, 2007.

(51) Int. Cl.
*A61K 48/00* (2006.01)
*A61K 39/02* (2006.01)
*A61K 39/106* (2006.01)
*C12P 1/04* (2006.01)
*C12N 1/20* (2006.01)

(52) U.S. Cl. .................. 424/93.2; 424/200.1; 424/234.1; 424/235.1; 424/261.1; 435/170; 435/252.3

(58) Field of Classification Search ........................ None
See application file for complete search history.

(56) References Cited

U.S. PATENT DOCUMENTS

| 5,672,345 | A | 9/1997 | Curtiss, III |
| 6,203,799 | B1 | 3/2001 | Mekalanos et al. |
| 2004/0208897 | A1 | 10/2004 | Curtiss et al. |
| 2007/0031458 | A1 | 2/2007 | Favre et al. |

OTHER PUBLICATIONS

Ryan et al. Infect. Immun. 65: 3118-3125, 1997.*
Leyton et al. Vaccine 23: 5120-5126, 2005.*
Ryan et al. Infect. Immun. 67: 1694-1701, 1999.*
Ryan et al. Infect. Immun. 68: 221-226, 2000.*
Clemens et al., Cross-Protection by B-Subunit-Whole Cell Cholera Vaccine Against Diarrhea Associated with Heat-Labile Toxin-Producing Enterotoxigenic *Escheria coli*: Results of a Large-Scale Field Trial, *J. Infect. Dis.*, 158(2): 372-377 (1988).
Clemens et al., Construction of a Potential Live Oral Bivalent Vaccine for Typhoid Fever and Cholera *Escherichia coli*-Related Diarrheas, *Infect. Immun.*, 46(2): 564-569 (1984).
Cohen et al., Randomized, controlled human challenge study of the safety, Immunogenicity, and protective efficacy of a single does of Peru-15, a live attenuated oral cholera vaccine, *Infect. Immun.*, 70(4): 1965-1970 (2002).
Glenn et al., Safety and Immunogenicity of an Enterotoxigenic *Escherichia coli* Vaccine Patch Containing Heat-Labile Toxin: Use of Skin Pretreatment to Disrupt the Stratum Corneum, *Infect. Immun.*, 75(5): 2163-2170 (2007).
Hall et al., Induction of systemic antifimbria and antitoxin antibody responses in Egyptian children and adults by an oral, kelled enterotoxigenic *Escherichia coli* plus cholera toxin B subunit vaccine, *Infect. Immune.*, 69(5): 2853-2857 (2001).
Holmgren et al., Mucosal immunity and vaccines, *Nature Medicine Supp.*, 11(4): S45-S53 (2005).
Kenner et al., Peru-15, an Improved Live Attenuated Oral Vaccine Candidate for *Vibrio cholerae* O1, *J. Infect. Dis.*, 172: 1126-1129 (1995).
Khan et al., Ability of SPI2 mutant of *S. typhi* to effectively induce antibody responses to the mucosal antigen enterotoxigenic *E. coli* labile toxin B subunit after oral delivery to humans, *Vaccine*, 25(21): 4175-4182 (2007).
Mekalanos et al., Cholera toxin genes: nucleotide sequence, delection analysis and vaccine development, *Nature*, 306: 551-557 (1983).
Mekalanos et al., Isolation of enterotoxin structural gene deletion mutations in *Vibrio cholerae* induced by two mutagenic vibriophages, *Proc. Natl. Acad. Sci., USA*, 79: 151-155 (1988).
Peltola et al., Prevention of travellers' diarrhoea by oral B-Subunit/whole-cell cholera vaccine, *Lancet*, 338(8778): 1285-1289 (1991).
Quadri et al., Enterotoxigenic *Escheria coli* in developing countries: epidemiology, microbiology, clinical features, treatment, and prevention, *Clin. Microbiol. Rev.*, 18(3): 465-483 (2005).
Sack et al., Evaluation of Peru-15, a New Live Oral Vaccine for Cholera, in volunteers, *J. Infect.Dis.*, 176(1): 201-205 (1997).
Sack et al., Randomised, double-blind, safety and efficacy of a killed oral vaccine for enterotoxigenic *E. Coli* diarrhoea of travelers to Guatemala and Mexico, *Vaccine*, 25(22): 4392-4000 (2007).
Scerpella et al., Safety, Immunogencicity, and Protective Efficacy of the Whole-Cell/Recombinant B Subunit (WC/rBs) Oral Cholera Vaccine Against Travelers' Diarrhea, *J. Travel. Med.*, 2(1): 22-27 (1995).
Sixma et al., Refined Structure of *Escherichia coli*, Heat-labile Enterotoxin, a close Relative of Cholera Toxin, *J. Mol. Biol.*, 230: 890-918 (1993).
Steffen, R., Epidemiology of Traveler's Diarrhea, *Clin. Infect. Dis.*, 41 Suppl.(8): S536-540 (2005).
Stratford et al., Optimization of *Salmonella enterica* Serovar Typhi ΔaroC ΔssaV Derivatives as Vehicles for Delivering Heterologous Antigens by Chromosomal Integration and in Vivo Inducible Promoters, *Infect. Immun.*, 73(1): 362-368 (2005).

\* cited by examiner

*Primary Examiner* — S. Devi
(74) *Attorney, Agent, or Firm* — Yankwich & Associates, P.C.; Leon R. Yankwich; Michael R. Wesolowski

(57) ABSTRACT

Oral immunogenic compositions imparting dual protection against enterotoxigenic labile toxin (LT)-expressing *Escherichia coli* (ETEC) and *Vibrio cholerae* based on the delivery of recombinant cholera toxin B antigen by attenuated, live bacterial vectors derived from *Vibrio cholerae* are disclosed. The compositions exhibit dual immunogenicity and retain the ability to colonize gastrointestinal mucosa-associated lymphoid tissues.

2 Claims, 7 Drawing Sheets

V. CHOLERAE HYPEREXPRESSING RECOMBINANT CHOLERA TOXIN B SUBUNIT SHOWING DUAL IMMUNOGENICITY

CROSS-REFERENCES TO RELATED APPLICATIONS

This application is a United States national stage filing under 35 U.S.C. §371 of international (PCT) application No. PCT/US2008/005261, filed Apr. 24, 2008 and designating the US, which international application claims priority to U.S. provisional application No. 60/926,123, filed Apr. 24, 2007.

FIELD OF THE INVENTION

The present invention relates to live attenuated bacterial vectors to deliver antigens for eliciting an immune response in a mammal against *Vibrio cholerae* and enterotoxigenic *E. coli* (ETEC). Immunogenic compositions providing neutralizing antibody responses to both *E. coli* antigens and *V. cholerae* are disclosed.

BACKGROUND OF THE INVENTION

Enterotoxigenic *E. coli* (ETEC) is recognized as one of the leading causes of infectious diarrhea in developing countries (see, e.g., Black, *Rev. Infect. Dis.,* 12 Suppl 1:S73-9 (1990)). The worldwide incidence of ETEC infections is estimated to result in 650 million cases of diarrhea and 380,000 deaths of children under the age of five (Gaastra et al., *Trends Microbiol.,* 4(11): 444-52 (1996)). ETEC is also an important cause of traveler's diarrhea responsible for up to 60% of all cases among people traveling to endemic regions in Mexico (Adachi et al., *J. Infect. Dis.,* 185(11):1681-3 (2002); Jiang et al., *J. Infect. Dis.,* 185(4):497-502 (2002); Bouckenooghe et al., *J. Travel. Med.,* 9(3):137-40 (2002)), Africa (Wolf et al., *J. Clin. Microbiol.,* 31(4):851-6 (1993)), Bangladesh (Qadri et al., *J. Clin. Microbiol.,* 38(1):27-31 (2000)), and Indonesia (Oyofo et al., *Am. J. Trop. Med. Hyg,* 65(2): 120-4 (2001)). ETEC is often linked to diarrheal outbreaks among American military personnel stationed abroad in Asia (Serichantalergs et al., *J. Clin. Microbiol.,* 35(6): 1639-41(1997)) and the Middle East (Wolf et al., 1993, supra). While generally self-limiting and treatable with antibiotics, ETEC infection can negatively affect the quality of life for those afflicted, often resulting in the loss of several days before normal activities can be resumed. This is of particular concern to members of the military deployed to less developed countries and to vacationers traveling to countries endemic for ETEC.

The majority of ETEC cases are caused by the ingestion of bacterial enteropathogens in contaminated food or drink. Upon ingestion, ETEC colonize the upper intestinal tract facilitated by a variety of colonization factors. Once infection is established, ETEC secrete either a heat labile toxin (LT), a heat stable toxin (ST) or both. Although these toxins are antigenically distinct and bind to different host receptors, both elicit the production of a profuse, watery diarrhea. Additional symptoms may include intestinal cramps, nausea and, occasionally, more severe symptoms such as vomiting and fever. Among the 7.5 to 10 million cases of traveler's diarrhea reported annually, roughly 2 million are caused by LT-expressing ETEC (Steffen, R., *Clin. Infect. Dis.,* 41 Suppl.(8): S536-40 (2005)).

ST is a small, monomeric toxin that contains multiple cysteine residues, whose disulfide bonds account for the heat stability of these toxins. There are two unrelated classes of STs that differ in structure and mechanism of action. Genes for both classes are found predominantly on plasmids, and some ST-encoding genes have been found on transposons.

LT is a prototypical A-B type toxin composed of an effector subunit (LT-A) and a cell-binding subunit (LT-B). LT-A is responsible for intoxication of host epithelial cells by activating host adenylate cyclase resulting in supraphysiological levels of cAMP. LT-B forms a pentameric complex that non-covalently interacts with LT-A to form LT holotoxin, which binds to the $GM_1$ ganglioside associated with lipid rafts present on the host cell surface (Hirst, *Cholera toxin and Escherichia coli heat-labile enterotoxin,* in: *The Comprehensive Sourcebook of Bacterial Protein Toxins,* Alouf and Freer, eds. (San Diego, Academic Press, 1999), pp. 104-29). Once LT is bound to a host cell and endocytosed, LT-A is delivered to the cell cytoplasm where it exerts its toxic effects, leading to the extrusion of chloride, bicarbonate and water from the cell and net fluid loss from the intestine.

Table 1 below shows the incidence of LT and ST-expressing ETEC strains isolated from travelers to various geographical regions around the world.

TABLE 1

| Location | Number of ETEC isolated | | | % LT total* |
|---|---|---|---|---|
| | #LT | #LT-ST | #ST | |
| Egypt | 12 | 25 | 20 | 65% |
| Saudi Arabia | 20 | 59 | 53 | 60% |
| Egypt | 16 | 17 | 42 | 44% |
| Jamaica | 22 | 6 | 10 | 74% |
| Kenya | 30 | 51 | 83 | 49% |
| India | 18 | 33 | 22 | 70% |
| Mexico | 91 | 53 | 51 | 74% |

% LT total = LT only + LT/ST strains

As can be seen from Table 1, the incidence of disease from ETEC strains that express LT varies widely and is dependent on geographical location. Worldwide, roughly half of all ETEC strains produce LT (Wolf, *Clin. Microbiol. Rev.,* 10(4): 569-84 (1997)). Native populations in endemic areas are often most afflicted by ST-producing strains (Qadri et al., 2000, supra; Oyofo et al., 2001, supra). This may be because, even when infection rates of LT-ETEC are high, the number of symptomatic infections can be reduced by prior exposure (Steinsland et al., *Lancet,* 362(9380):286-91 (2003)), leading to the observation that the rate of asymptomatic infections by LT producing strains is typically greater than for ST producing strains (Qadri et al., *Clin. Microbiol. Rev.,* 18(3):465-83 (2005)).

Travelers from the developed world to endemic regions develop ETEC infections of a different profile. In many areas of the world, LT-producing ETEC (LT only and LT-ST) are responsible for most cases of traveler's diarrhea (Bouckenooghe et al., 2002, supra; Wolf et al., 1993, supra; Estrada-Garcia, *J. Travel. Med.,* 9(5):247-50 (2002); Rockabrand et al., *Diagn. Microbiol. Infect. Dis.,* 55(1):9-12 (2006); Steffen et al., *J. Travel. Med.,* 12(2):102-7 (2005)). It is clear from this distribution that a vaccine against LT-producing strains would protect travelers to many endemic areas against ETEC-related diarrhea.

The LTs of *E. coli* are oligomeric toxins which are closely related in structure and function to the cholera enterotoxin (CT) expressed by *Vibrio cholerae* (Sixma et al., *J. Mol. Biol.,* 230:890-918 (1993)). Like LT, CT is composed of a single A subunit (CT-A) and a pentamer forming B subunit (CT-B) that binds $GM_1$ ganglioside. LT and CT share many characteristics, including holotoxin structure, protein sequence (ca. 80% identity), primary receptor identity, enzymatic activity, and activity in animal and cell culture assays. LT and CT are additionally antigenically cross-reactive (Hirst, 1999, supra).

Attenuated *Salmonella typhi* has been used to deliver the B subunit of enterotoxinogenic *E. coli* (LT-B) (Stratford et al., *Infect. Immun.* 73(1):362-8 (2005)). The construct consisted of a single chromosomal copy of eltB expressed from the ssaG promoter. Mice inoculated subcutaneously or intranasally reportedly developed high titer responses to LT-B. In a Phase I clinical study, it was reported that 67% of vaccinees seroconverted after two doses (Khan et al., *Vaccine*, 25(21): 4175-82 (2007). It was noted, however, that in a similar construct, most of the LT-B was cell-associated, and release into the surrounding media was achieved only with cell lysis (Clements et al., *Infect. Immun.* 46(2):564-9 (1984)). Since the immunogenicity of LT-B and CT-B are associated with their ability to interact with host surface receptors (Nashar et al., *Proc. Natl. Acad. Sci. USA*, 93(1):226-30 (1996)), it is possible that a strain able to secrete LT-B or CT-B would be more effective for raising an anti-LT-B/anti-CT-B immune response. One object of the present invention is to discover whether this increased immunogenicity can be achieved.

Purified LT has also been tested as an ETEC vaccine. Although toxic when delivered orally and intranasally, transcutaneous delivery has shown potential. In a recent study, volunteers were vaccinated twice over a 21-day period by wearing an arm patch loaded with 50 μg of LT for 6-8 hours. All vaccinees reportedly seroconverted and developed a mean increase in serum IgG titers against LT of 24-fold (Glenn et al., *Infect. Immun.*, 75(5):2163-70 (2007)). Neutralizing antibody against LT was also reportedly detected. In a subsequent study, subjects were vaccinated three times, on days 0, 21, and 42 by application of an arm patch, alternating arms with each visit (McKenzie et al., *Vaccine*, 25(18):3684-91 (2007)). Each subject then returned 18-26 hours later for patch removal. Subjects were then challenged with a wild-type ETEC strain. Although all of the vaccinees had seroconverted to LT, no protection against an LT/ST ETEC challenge was observed.

Orally delivered killed ETEC is another approach that has been attempted but has failed to show induction of protective immunogenicity: In a recent field study, an orally delivered killed vaccine was used, consisting of a combination of several ETEC strains, each expressing a different colonization factor, and 1 mg of CT-B per dose (Sack et al., *Vaccine*, 25(22):4392-400 (2007)). Travelers receiving two doses were monitored for several weeks after traveling to Mexico or Guatemala. No protection against vaccine-preventable diarrhea was observed, although the severity of disease was reportedly reduced in vaccinees.

Such studies indicate a possible utility for CT-B to promote cross-over immunity against LT/ETEC strains. However, they also dramatically illustrate the failure of previous vaccines to deliver CT-B by a route or in a form or quantity that would provide a useful level of anti-LT immunity.

Like ETEC, *Vibrio cholerae*, the causative agent of cholera, has long plagued mankind. There have been six pandemics of this disease caused by strains of *V. cholerae* belonging to the "Classical" biotype. The etiological agents of the current (seventh) pandemic belong to the "El Tor" biotype. Recently the seventh pandemic has extended to a new locale, that of South America. Beginning in January of 1991, an epidemic of cholera resulted in more than 250,000 cases and over 2,000 deaths in Peru, Ecuador, Columbia, and Chile. In November of 1992, an antigenically distinct, non-01 form of *V. cholerae* emerged in India and Bangladesh and within eight months caused an estimated 500,000 new cholera cases and 6,000 deaths. The pandemic potential of this new strain, designated serogroup 0139 synonym "Bengal", seems assured and is a new cause of concern throughout the developing world.

Because natural infection by and recovery from cholera induces immunity lasting at least 3 years (Tacket et al., Cholera Vaccines, in *Vaccines: New Approaches to Immunological Problems*, Ellis, R. W., ed. (Butterworth-Heinenann, Boston, 1992); Levine et al., *J. Infect. Dis.*, 143:818-820 (1981)), much effort has been made to produce a live, attenuated cholera vaccine that when administered orally would mimic the disease-producing wild type strains in its immunization properties but would not cause adverse symptoms or reactions in the immunized individual, i.e., display low reactogenicity. Attempts at developing vaccines of this type typically have involved deletion mutations that inactivate the gene encoding the A subunit of cholera toxin, a protein which is responsible for most of the diarrhea seen in this disease (Mekalanos et al., *P.N.A.S. USA*, 79:151-155 (1988); Mekalanos et al., *Nature*, 306:551-557 (1983); Kaper et al., *Nature*, 308:655-658 (1984); Kaper et al., *Biotechnology*, 2:345 (1984)). While both oral, killed whole cell vaccines and several live, attenuated cholera vaccines have been developed, the most promising of these provide little protection against the El Tor biotype of *V. cholerae* and probably no protection against the 0139 serotype.

*V. cholerae* only causes disease when colonization of the small bowel occurs. As a mucosal pathogen, *V. cholerae* adheres selectively to the M cells of the gastrointestinal tract (Owen et al., *J. Infect. Dis.*, 153:1108-1118, (1986)) and is a strong stimulus to the mucosal immune system (Svennerholm et al., *Lancet*, 1:305-308, (1982)). This colonization of mucosa-associated lymphoid tissues (MALT) is also required for the induction of a localized immune response featuring locally produced secretory IgA, an important aspect of development of effective vaccines. (Holmgren & Czerkinsky, *Nature Medicine Supp.*, 11(4):S45-S53 (2005).) Because of the importance of eliciting mucosal immunity in combating *V. cholerae* (and ETEC) infections, live avirulent vaccine strains are of particular interest: killed vaccines, although they might be highly immunogenic, do not have the ability to colonize gut or mucosa-associated tissues. A promising candidate for an effective live avirulent cholera vaccine is CholeraGarde® Peru-15 (under development by AVANT Immunotherapeutics, Inc., Needham, Mass.). Peru-15 is a live avirulent *V. cholerae* strain (genotype: ΔattRS1, Δcore ΔrecA:htpG:ctxB, Δctxφ) that has been shown to be well-tolerated and immunogenic in more than 400 subjects (U.S. Pat. No. 6,203,799; Kenner et al., *J. Infect. Dis.* 172:1126-1129 (1995); Cohen et al., *Infect. Immun.* 70: 1965-1970 (2002)).

An oral, killed, whole-cell cholera vaccine, Dukoral®, which includes the addition of 1 mg CT-B, was developed in the 1980s by SBL Vaccin of Sweden. While evaluating the efficacy of this vaccine against cholera in Bangladeshi women and children, it was discovered that the vaccine also provided short-term protection against LT/ST-producing ETEC and that protection was dependent on the inclusion of CT-B in the vaccine (Clemens et al., *J. Infect. Dis.*, 158(2): 372-7 (1988)).

In a later study, Finnish tourists traveling to Morocco received two doses of Dukoral® and were protected against disease caused by LT and LT/ST-expressing ETEC (Peltola et al., *Lancet*, 338(8778):1285-9 (1991)). Specifically, the WC/rBS cholera vaccine (Dukoral®) was reported to prevent 23% of all diarrhea episodes and 52% of episodes due to ETEC in Finnish tourists visiting Morocco. This protection was reported, however, not to last more than a few months. While the short-term protection was limited, these studies show CT-B as a possibly effective immunogen in the prevention of diarrhea against LT-producing ETEC in travelers.

As seen from the foregoing, many attempts have been made to address ETEC and *V. cholerae* infections and to provide protection against debilitating diseases for people living in or planning travel to endemic areas. However, the need remains for a composition that is effective to elicit an effective mucosal immune response to ETEC or *V. cholerae*, or ideally there is a great need for an immunogenic composition that would have the ability to raise a dual immune response, capable of eliciting neutralizing antibodies against both *V. cholerae* and ETEC pathogens. Potential vaccine strains providing dual immunogenicity in the form of a live, attenuated strain that could be administered orally and that retain the ability to colonize MALT tissues would be especially desirable.

SUMMARY OF THE INVENTION

The present invention provides an immunogenic composition for generating a dual immune response against *V. cholerae* and enterotoxigenic *Echerichia coli* (ETEC). The immunogenic composition of the present invention comprises a live attenuated *V. cholerae* bacterium engineered to produce high levels of the cholera toxin B subunit (CT-B). Strains according to the invention are able to produce and secrete high levels of CT-B and to elicit, in turn, a neutralizing anti-LT response and also retain the ability to colonize mucosa-associated lymphoid tissues (MALT) eliciting, in turn, a neutralizing vibriocidal antibody response. Advantageously, the cholera toxin B subunit is preferably expressed by transforming an attenuated *V. cholerae* host with a multi-copy expression plasmid capable of generating large amounts of CT-B. The discovery of a high CT-B-expressing strain in which the hyperexpression of CT-B is not toxic to the bacterial host cell is surprising and beneficial. One particular such strain, Peru-15(pCTB), is described in detail below.

The present invention provides for an immunogenic composition comprising a live, attenuated *V. cholerae* bacterium having a recombinant antigen-expressing, multi-copy plasmid, wherein said antigen is cholera toxin B (CT-B).

Preferably, the immunogenic composition comprising a live attenuated *V. cholerae* bacterium contains a mutation in a genetic locus in the chromosome of said bacterium wherein said mutation prevents expression from said genetic locus of a functional protein, and wherein said plasmid contains a functional copy of the gene encoding that protein, thereby complementing the mutation in the chromosome of said microbe. Where the mutation is lethal to the bacterial cell in the absence of the complementing plasmid-based gene, the recombinant or transformed bacterium embodies a "balanced-lethal" system, which maintains the viability of the transformant only so long as the balancing plasmid is retained. Accordingly, the balanced-lethal system provides a selection mechanism for transformed bacteria retaining the expression plasmid housing the complementary gene.

A particularly useful gene to be used for such plasmid complementation for use in the immunogenic composition comprising the live attenuated *V. cholerae* bacterium is the gene for glutamine synthetase, i.e., the GlnA gene. Other balancing genes are also suitable, including but not limited to asd, purB, thya, and the like.

Compositions of the present invention may be prepared using any strain of *V. cholerae* that can be used for enteral immunization to elicit a mucosal anti-*V. cholerae* response. The strain may be of any biotype, i.e., Classical or El Tor. A particularly useful biotype, in view of the nature of current infections worldwide, will be *V. cholerae* bacteria of the El Tor biotype.

Compositions of the present invention may be prepared using a *V. cholerae* strain of any serotype, e.g., Inaba, 0139 or Ogawa serotype. A preferred strain for use according to the present invention is Peru-15 (ATCC 55635).

The *V. cholerae* host strain according to the present invention is transformed to express excess cholera toxin B subunit (CT-B). Preferably the host strain will be transformed with a plasmid for directing expression of CT-B in the host at high levels, and most preferably the CT-B is expressed in a form that is secreted by the host cells. A Peru-15 cell line (live attenuated *V. cholerae*) further having a deletion in the native GlnA gene and bearing the multi-copy expression plasmid, pMEG-2350, which includes a GlnA operon supplementing the chromosomal GlnA deletion and also includes the coding sequence for CT-B under control of the Ptrc promoter, has been prepared. This strain is referred to herein by the designation Peru-15(pCTB).

Peru-15(pCTB) overexpresses CT-B but also retains the ability to colonize the MALT and exhibits the ability to elicit both vibriocidal and anti-LT neutralizing antibodies, in high titer. Samples of Peru-15(pCTB) have been deposited under the conditions of the Budapest Treaty with the American Type Culture Collection (ATCC), 10801 University Boulevard, Manassas, Va. 20110 USA (ATCC® Patent Deposit Designation PTA-9130).

The present invention also provides a method for eliciting in a mammalian subject a dual immune response characterized by the production of neutralizing antibodies recognizing *V. cholerae* and ETEC antigens, the method comprising administering to a mammal an immunogenic composition according to the invention.

The present invention also provides a method for protecting a susceptible host against an infection of ETEC and/or *V. cholerae* comprising inoculating said host with an amount of an immunogenic composition according to the invention sufficient to invoke an anti-LT and/or anti-*V. cholerae* immune response, where protecting said host means that LT-neutralizing and/or vibriocidal antibodies are produced after such inoculation, such that development of disease as the result of ETEC or *V. cholerae* infection is prevented or reduced in severity in comparison to an uninoculated subject. The data presented herein pertaining to the immunogenic compositions of the present invention indicate that embodiments of the present invention will be suitable for immunizing human subjects against either or both of ETEC and *V. cholerae*.

BRIEF DESCRIPTION OF THE DRAWINGS

FIG. 2(A) shows the Coomassie stained gel; FIG. 2(B) shows the Western blot probed with anti-CT-B. Lane 1 shows low molecular weight makers; Lane 2 is Peru-15; Lane 3 is Peru-15(pCTB); and Lane 4 is purified CT-B (1 µg loaded in (A) and 0.1 µg loaded in (B)). Pentamerization of secreted CT-B was confirmed by electrophoresing supernate samples with and without heating, shown in FIG. 2(C). Unheated samples ran as a large complex that was disrupted by heating as expected for pentameric CT-B. Lanes 1 and 8 are high molecular weight rainbow markers; Lanes 2 and 7 are 0.1 µg CT-B; Lanes 3 and 6 are Peru-2; and Lanes 4 and 5 are Peru-15(pCTB).

DEFINITIONS

Figure 1:
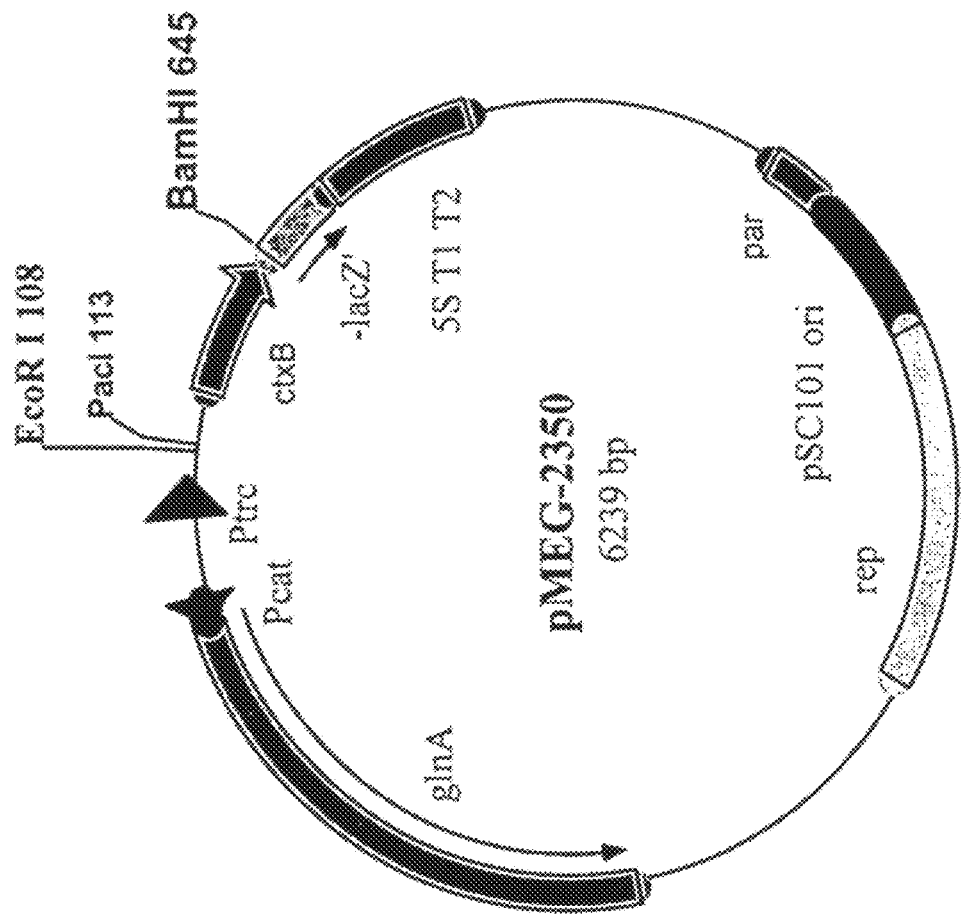
FIG. 1 is a plasmid map of pMEG-2350, a high copy number plasmid (pSC101 ori) with the CT-B gene placed under the control of the strong constitutive Trc promoter (Ptrc). A copy of GlnA is present on the plasmid to compensate for the knockout of GlnA on the chromosome.

In order that the invention may be more fully understood, the following terms are defined.

As used herein, "attenuated", "attenuation", and similar terms refer to elimination or reduction of the natural virulence of a bacterium in a particular host organism, such as a mammal. "Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium.

As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, regulatory site (including transcriptional terminator sites, ribosome binding sites, transcriptional inhibitor binding sites, transcriptional activator binding sites), origin of replication, intercistronic region, and portions therein. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis.

As used herein, the term "infection" has the meaning generally used and understood by persons skilled in the art and includes the invasion and multiplication of a microorganism in or on a host organism ("host", "individual", "patient") with or without a manifestation of a disease (see, "virulence" above). Infectious microorganisms include pathogenic bacteria, such as *Vibrio cholerae* and enterotoxigenic *E. coli* (ETEC), which can cause serious diseases when infecting an unprotected individual. An infection may occur at one or more sites in or on an individual. An infection may be unintentional (e.g., unintended ingestion, inhalation, contamination of wounds, etc.) or intentional (e.g., administration of a live vaccine bacterial strain, experimental challenge with a pathogenic bacterial strain). In a vertebrate host organism, such as a mammal, a site of infection includes, but is not limited to, the respiratory system, the alimentary canal (gut), the circulatory system, the skin, the endocrine system, the neural system, and intercellular spaces. Some degree and form of replication or multiplication of an infective microorganism is required for the microorganism to persist at a site of infection. However, replication may vary widely among infecting microorganisms. Accordingly, replication of infecting microorganisms comprises, but is not limited to, persistent and continuous multiplication of the microorganisms and transient or temporary maintenance of microorganisms at a specific location. Whereas "infection" of a host organism by a pathogenic microorganism is undesirable owing to the potential for causing disease in the host, an "infection" of a host individual with a live vaccine comprising genetically altered, attenuated *Vibrio cholerae* bacterial strain as described herein is desirable because of the ability of the bacterial strain to elicit a protective immune response to antigens of *Vibrio cholerae* and enterotoxigenic *E. coli* (ETEC) bacteria that cause infectious diarrhea in humans.

As used herein, the terms "disease" and "disorder" have the meaning generally known and understood in the art and comprise any abnormal condition in the function or well being of a host individual. A diagnosis of a particular disease or disorder, such as infectious diarrhea, by a healthcare professional may be made by direct examination and/or consideration of results of one or more diagnostic tests.

A "live immunogenic composition", a "live dual immunogenicity composition", or a "live bacterial immunogenic composition" according to this invention, or similar terms, refer to a composition comprising a live strain of *Vibrio cholerae* bacteria which has been altered using genetic engineering techniques to be (1) avirulent (attenuated) in comparison to wild type *V. cholerae* stains that are capable of inducing cholera and (2) capable of expression (preferably hyperexpression) and secretion of a recombinant cholera toxin B subunit polypeptide (CT-B) in amounts greater than (i.e., at least 10-fold greater than, preferably at least 25-fold greater than, more preferably at least 50-fold, greater than) the CT-B expression level of the native *V. cholerae* strain from which the altered strain according to the invention is derived, which altered strain is capable of eliciting an immune response when administered to a mammalian subject having a dual efficacy, namely, eliciting an antibody response that is vibriocidal (i.e., mediates killing of *V. cholerae* pathogens) or neutralizes cholera toxin, and also neutralizes ETEC heat-labile toxin (i.e., a neutralizing anti-LT response). Preferred exemplars of *V. cholerae* strains according to the invention elicit mucosal immunity, and preferably compositions according to the invention are effective when administered enterally, especially orally.

The altered *V. cholerae* strains of the present invention are good candidates for human vaccines providing protection against *V. cholerae* and ETEC infection. As used herein "providing protection" against *V. cholerae* and/or ETEC infection or reference to "an immunoprotective composition" according to the invention, means that at least a partial immunity to cholera and/or ETEC is imparted, that is, an immunity that is effective to prevent manifestation of the associates disease when *V. cholerae* or ETEC infection occurs or that is effective to lessen the severity of the disease in comparison to non-immunized subjects exposed to the same *V. cholerae* or ETEC pathogen. Such at least partial immunity may be evidenced by any of a variety of observable or detectable conditions, including but not limited to, diminution of one or more disease symptoms (e.g., diarrhea, fever, pain, bleeding, inflammation of lymph nodes, weakness, malaise), shorter duration of illness, diminution of tissue damage, regeneration of healthy tissue, clearance of pathogenic microorganisms from the individual, and increased sense of well being by the individual. Although highly desired, it is understood by persons skilled in the art that no immunogenic composition is expected to induce complete protection from a disease in every individual that is administered the composition or that protective immunity is expected to last throughout the lifetime of an individual without periodic "booster" administrations of an immunogenic composition. It is also understood that a live immunogenic composition comprising a bacterium described herein may be, at the discretion of a healthcare professional, administered to an individual who has not presented symptoms of infectious diarrhea but is considered to be at risk of infection or is known to already have been exposed to *V. cholerae* or enterotoxigenic *E. coli* bacteria, e.g., by travel, proximity or contact with infected patients or bacterially contaminated air, liquids, or surfaces.

The terms "enteral", "enterally", "non-parenteral", "non-parenterally", and the like, refer to administration of a compound or composition to an individual by a route or mode along the alimentary canal. Enteral administration encompasses oral, sublingual, buccal, nasopharyngeal, esophageal, gastrointestinal, and rectal routes of administration. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition. An example of rectal administration include, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous and/or endogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

The term "balanced-lethal host vector system" or "balanced-lethal system" refers to a technique for maintaining a plasmid in a population of transformed cells, as described, for instance, in U.S. Pat. No. 5,672,345, incorporated by reference. In general, a balanced-lethal system is characterized by genetically engineered host cells which can be maintained as a genetically stable population, wherein the host cells express a desired recombinant gene product. The host cells in this population characteristically have had inactivated a native gene encoding a product, such as an enzyme, which is essential for cell survival. For example, deletion or disablement of a gene coding on expression for an enzyme catalyzes a step in the biosynthesis of an essential component, such as the cell wall is a good selection for the deletion target of a balanced-lethal system. In addition, the function of the deleted or disabled native gene is replaced by a recombinant gene, introduced, e.g., on a plasmid expression vector, whereby the expression of recombinant gene supplies the essential gene product, permitting survival of the cell. Thus, only transformed host cells that maintain the balancing plasmid will remain viable. Advantageously, the plasmid also contains an expression system for intracellular production of a desired gene product or preferably the expression of the essential gene products is operably linked to the expression of the desired gene product. In the present invention, the desired gene product is recombinant CT-B, and a balanced-lethal host vector system advantageously allows production of the recombinant CT-B from a plasmid vector that is maintained in the transformed cells by the balanced-lethal system. The term "balanced-lethal expression vector" refers to an expression plasmid that is capable of directing expression in a host cell of a desired product, in this case recombinant CT-B, which also is capable to directing expression of a balancing gene corresponding to a deleted or disable gene of the host chromosome.

References to the "expression of recombinant CT-B" mean expression by means of genetic manipulation of the host cell of cholera toxin B subunit or an immunogenic portion thereof by virtue of exogenous genetic material introduced into the host cell and does not refer to and excludes expression of native cholera toxin B expressed naturally due to any unaltered chromosomal cholera toxin B subunit genetic locus that may exist or remain in the host cell.

The definitions of other terms used herein are those understood and used by persons skilled in the art and/or will be evident to persons skilled in the art from usage in the text.

DETAILED DESCRIPTION OF THE INVENTION

The present invention provides an immunogenic composition for generating a dual immune response against *V. cholerae* and enterotoxigenic *Echerichia coli* (ETEC). The immunogenic composition of the present invention comprises a live attenuated *V. cholerae* bacterium transformed to express recombinant cholera toxin B (CT-B). In preferred features, the immunogenic compositions of the present invention comprise genetically altered strains of *Vibrio cholerae* which have been attenuated to be avirulent and transformed so as to express and preferably secrete recombinant CT-B. It has been discovered that immunogenic compositions according to the present invention:

are able to colonize gastrointestinal MALT and elicit production of secretory IgA immunoglobulins, an indicator of the development of desired mucosal immunity, are able to express high levels of immunogenic CT-B polypeptides, e.g., at levels that exceed by at least 10-fold the CT-B production of the parental strain of *Vibrio cholerae* from which the attenuated transformant *Vibrio cholerae* of the invention is prepared or of wild-type pathogenic *Vibrio cholerae* strain, are able to express such levels of CT-B without toxicity to the bacterial host cells, so that survivability of the cells necessary for MALT colonization is retained, are able to elicit production of anti-*V. cholerae* antibodies including anti-CT-B antibodies, which anti-CT-B antibodies recognize LT, where such antibody response is not only cross-reactive with LT but is a neutralizing antibody response (i.e., the reactive antibodies are active to promote the clearance or neutralization of LT toxin function), and where, moreover, the anti-*V. cholerae* antibody response includes vibriocidal antibodies, thus making the compositions exhibit a dual immunogenicity, i.e., against both *Vibrio cholerae* and ETEC antigens.

Compositions of the present invention may be prepared using any avirulent strain of *V. cholerae* that can be used for enteral immunization to elicit a mucosal anti-*V. cholerae* response. It is important that the strain selected remain viable long enough to colonize the gastrointestinal MALT and elicit the production of immunoglobulins, yet remain avirulent and non-reactogenic within the host subject so as not to induce intolerable disease symptoms. The strain may be of any biotype, i.e., Classical or El Tor. Compositions of the present invention may be prepared using a *V. cholerae* strain of any serotype, e.g., Inaba, 0139 or Ogawa serotype.

*Vibrio cholerae* bacteria have been recognized as being particularly useful as live "host" vectors for orally administered vaccines because these bacteria are enteric organisms that, when ingested, can infect and persist in the gut (especially the intestines) of humans and animals. Accordingly, when orally administered to an individual, live *V. cholerae* bacteria that are genetically engineered to over-express CT-B as described herein have the inherent ability to establish a population (infection) in the gut and, thereby, provide a desirable source of immunogenic CT-B antigen polypeptide to elicit an immune response in the mucosal tissue of the individual. As a variety of *V. cholerae* bacteria are known to be highly virulent to most hosts, e.g., causing cholera or severe diarrhea in humans and other mammals, the virulence of *V. cholerae* bacterial strains toward an individual that is targeted to receive a vaccine composition must be attenuated. Attenuation of virulence of a bacterium is not restricted to the elimination or inhibition of any particular mechanism and may be obtained by mutation of one or more genes in the *V. cholerae* genome (which may include chromosomal and non-chromosomal genetic material). Thus, an "attenuating mutation" may comprise a single site mutation or multiple mutations that may together provide a phenotype of attenuated virulence toward a particular host individual who is to receive a live vaccine composition.

In recent years, a variety of *V. cholerae* have been developed that are attenuated for pathogenic virulence in an individual and thus proposed as useful for developing various live bacterial vaccines (see, e.g., U.S. Pat. Nos. 6,203,799; 5,631,010; 5,874,088; 6,036,953; all incorporated herein by reference). In the case of strains of *Vibrio cholerae*, mutations to stably eliminate the ability of the organism to produce functional cholera toxin have been the focus of attenuation efforts. Thus, elimination of at least the CT-A subunit, by deleting or disabling the ctxA gene, have been of primary importance, coupled with additional deletions or mutations to render the ctxA mutation permanent and irreversible. Thus, companion deletions of recA genes, RS (long repeat) sequences, and att phage attachment sites at all occurrences in the genome are especially advantageous. The ctxB gene encoding CT-B also may be deleted to reduce virulence; however, since in the absence of CT-A a functional cholera toxin is not formed, and since CT-B itself is usefully immunogenic, the gene for CT-B may be advantageously retained, or, as in the case of the present invention, introduced into the host using genetic engineering techniques to produce excess recombinant CT-B as a supplemental immunogen. Peru-15, for example, is attenuated by a large genetic deletion taking the entire ctx genetic element out of the genome, but ctxB is reinserted into the recA gene, by way of disabling the recA function while retaining some CT-B expression for the sake of antigen presentation. See, e.g., U.S. Pat. No. 6,203,799, incorporated herein by reference. Moreover, our experiments indicate that the increased amount of CT-B secreted by vaccine candidates according to this invention also acts as somewhat of an adjuvant in mucosal immunization.

A number of live, avirulent *V. cholerae* vaccine strains have been disclosed in the literature which may be used in creating the immunogenic composition for generating a dual immune response against *V. cholerae* and enterotoxigenic *Escherichia coli* (ETEC) as disclosed herein. A preferred strain for use according to the present invention is Peru-15 (ATCC 55635); however, additional preferred strains which may be used are disclosed in U.S. Pat. No. 5,874,088, e.g., Peru-2, Peru-3, Peru-4, Peru-5, Bang-2, Bang-3, Bang-5 Bah-2, Bah-4, or Bah-5.

As noted above, it is important that the selected strain is avirulent, or is genetically altered to be avirulent. Mutant strains according to the invention optionally include additional mutations introduced to improve the safety (e.g., stable avirulence) and/or the immunogenicity of the vaccine. Such additional mutations include, but are not limited to, inactivation of one or more genes involved in DNA recombination, for example the recA gene and all att phage attachment sites found in the genome (see, e.g., WO 95/18633).

As previously noted, it is important that the selected *V. cholerae* strain be able to elicit mucosal immunity in combating *V. cholerae* (and ETEC) infections, therefore live avirulent vaccine strains are of particular interest. As a mucosal pathogen, *V. cholerae* adheres selectively to the M cells of the gastrointestinal tract (Owen et al., 1986, supra) and is a strong stimulus to the mucosal immune system (Svennerholm et al., 1982, supra). This colonization of mucosa-associated lymphoid tissues (MALT) is particularly effective for in the induction of a localized immune response featuring locally produced secretory IgA, an important aspect of development of effective vaccines against such pathogens as ETEC and *V. cholerae*. (Holmgren & Czerkinsky, 2005, supra.)

Peru-15 has been shown to be well-tolerated (i.e., non-reactogenic) and immunogenic, inducing a strong localized immune response featuring locally produced secretory IgA, in more than 400 subjects (U.S. Pat. No. 6,203,799; Kenner et al., *J. Infect. Dis.* 172:1126-1129 (1995); Cohen et al., *Infect. Immun.* 70: 1965-1970 (2002)), and therefore is a particularly preferred strain.

In preferred features, the immunogenic compositions of the present invention not only comprise genetically altered strains of *Vibrio cholerae* which have been attenuated, but are also transformed so as to express, or hyper-express, recombinant CT-B. Even more preferably, the live attenuated dually immunogenic strain maintains its native ability to secrete CT-B.

CT-B has proven to be an effective antigen in eliciting an immunogenic response against *V. cholerae* (U.S. Pat. No. 6,203,799; cf., also, Dukoral®), and also ETEC. This is because the heat-labile toxin (LT) of *E. coli* is an oligomeric toxin closely related in sequence to the cholera enterotoxin (CT) expressed by pathogenic *Vibrio cholerae* (Sixma et al., 1993, supra). Like LT, CT is composed of a single A subunit (CT-A) and a pentamer-forming B subunit (CT-B) that binds $GM_1$ ganglioside. LT and CT share many characteristics, including holotoxin structure, protein sequence (>80% sequence identity), primary receptor identity, enzymatic activity, and activity in animal and cell culture assays. Additionally, LT and CT are partially antigenically cross-reactive (Hirst, 1999, supra).

In view of this possibility of inducing the production of antibodies exhibiting CT/LT cross-reactivity, we have prepared an attenuated *V. cholerae* expressing increased amounts of CT-B, while maintaining other advantageous properties of the immunogenic host, to provide a vaccine candidate for generating a dual immune response against *V. cholerae* and enterotoxigenic *Echerichia coli* (ETEC) and thus providing a single strain capable of imparting immunoprotection to infections by both *V. cholerae* and ETEC pathogens.

Methods of transforming bacterial host cells to cause expression of a recombinant protein of interest are well known in the art. Preferably, for the immunogenic compositions of the present invention, transformation of *V. cholerae* host cells is accomplished by introduction of an expression plasmid capable of directing expression within the host cells of CT-B. In preferred features, the structural gene encoding CT-B immunogen includes coding sequence for secretion signals, so that soluble CT-B is excreted from the host cells. In further embodiments, expression of the CT-B immunogen is under control of a powerful constitutive promoter, such as Ptrc, so that constant production (and secretion) of the CT-B immunogen occurs after infection of an inoculated subject. In further preferred embodiments, the *V. cholerae* host has a knock-out (deletion or disablement) in its chromosome of an essential gene, such as glnA, and the plasmid CT-B expression vector also includes a functional complementary gene (e.g., glnA) to balance the lack of that gene in the chromosome, thus providing selective pressure for retention of the expression plasmid as the cells replicate, otherwise known as a balanced-lethal host vector system.

Preferably, CT-B expression plasmids useful in the invention are engineered to over-express and secrete CT-B in a host *V. cholerae* strain. An expression plasmid in the bacterial strains described herein may also contain one or more transcriptional terminators adjacent to the 3' end of a particular nucleotide sequence on the plasmid to prevent undesired transcription into another region of the plasmid. Such transcription terminators thus serve to prevent transcription from extending into and potentially interfering with other critical plasmid functions, e.g., replication or balancing gene expression. Examples of transcriptional terminators that may be used in the antigen-encoding plasmids described herein include, but are not limited to, the T1 and T2 transcription terminators from 5S ribosomal RNA bacterial genes (Brosius and Holy, *Proc. Natl. Acad. Sci. USA,* 81: 6929-6933 (1984); Brosius, *Gene,* 27(2): 161-172 (1984); Orosz et al., *Eur. J. Biochem.,* 201(3):653-659 (1991)).

The expression plasmids may be maintained in an attenuated bacterial host strain by employing the balanced-lethal system based on complementation of a mutation in a chromosomal gene as previously described by Ryan et al., *Infect. Immun.,* 68(1):221-6 (2000) (see, also, Nakayama et al., *Bio/Technology,* 6:693-697 (1988) and U.S. Pat. No. 5,672,345, incorporated by reference). As previously noted, a balanced-lethal system is characterized by genetically engineered host cells which can be maintained as a genetically stable population, wherein the host cells express a desired recombinant gene product. The host cells in this population characteristically have an inactivated native gene encoding a product, such as an enzyme, which is essential for cell survival. In addition, the function of the deleted or disabled native gene is replaced by a recombinant gene, introduced on a plasmid expression vector, whereby the expression of recombinant gene supplies the essential gene product, permitting survival of the cell. Thus, only transformed host cells that maintain the balancing plasmid will remain viable. Preferably, the plasmid also contains an expression system for production of a desired gene product or preferably the expression of the essential gene products is operably linked to the expression of the desired gene product. In the present invention, the desired gene product is recombinant CT-B, and a balanced-lethal host vector system advantageously allows production of the recombinant CT-B from a plasmid vector that is maintained in the transformed cells by the balanced-lethal system.

The CT-B-expressing plasmids described herein comprise one or more nucleotide sequences that encode CT-B or an immunogenic portion thereof that elicits production of antibodies immunologically cross-reactive with LT. The coding sequence for CT-B is known. See, Mekalanos et al., *Nature,* 306:551-57 (1983). Such coding sequences are operably linked to a promoter of transcription that functions in a *Vibrio cholerae* bacterial strain when such strain is ingested or otherwise administered to a mammalian subject. A variety of naturally occurring, recombinant, and semi-synthetic promoters are known to function in enteric bacteria, such as λPR (lambda phage), and promoters from phages P22 and T4. Promoters (P) that are useful in the invention include, but are not limited to, well known and widely used promoters for gene expression such as the naturally occurring Plac of the lac operon and the semi-synthetic Ptrc (see, e.g., Amman et al., *Gene,* 25(2-3):167-178 (1983)) and Ptac (see, e.g., Amann et al., *Gene,* 69(2):301-315 (1988)).

Some promoters are known to be regulated promoters that require the presence of some kind of activator or inducer molecule in order to initiate transcription of a coding sequence to which they are operably linked. However, some promoters may be regulated or inducible promoters in *E. coli,* but function as unregulated promoters in *V. cholerae.* An example of such a promoter is the well known trc promoter ("Ptrc", see, e.g., Amman et al., 1983, supra). As with Plac and Ptac, Ptrc functions as an inducible promoter in *Echerichia coli* (e.g., using the inducer molecule isopropyl-β-D-thio-galactopyranoside, "IPTG"), however, in *V. cholerae* bacteria having no LacI repressor, Ptrc is an efficient constitutive promoter that readily directs transcription of structural genes encoding CT-B polypeptides present on plasmids described herein. Accordingly, such a constitutive promoter does not depend on the presence of an activator or inducer molecule to cause expression of CT-B antigen in a strain of *V. cholerae.*

The CT-B expression plasmids useful in the present invention also contain an origin of replication (ori) that enables the plasmids to be maintained as multiple copies in the bacterial cell. A number of multi-copy plasmids that replicate in *V. cholerae* bacteria are known in the art, as are various origins of replication for maintaining multiple copies of plasmids. Preferred origins of replication for use in the multi-copy antigen-expressing plasmids described herein include the origin of replication from the multi-copy plasmid pBR322 ("pBR ori"; see, e.g., Maniatis et al., in *Molecular Cloning: A Laboratory Manual* (Cold Spring Harbor Laboratory, Cold Spring Harbor, 1982), pp. 479-487; Watson, *Gene,* 70: 399-403, 1988) and the origin of replication of pUC plasmids ("pUC ori"), such as found on plasmid pUC18 (see, e.g., Yanish-Perron et al., *Gene,* 33:103-119 (1985)).

As previously noted, it is particularly preferred that the strains of the invention disclosed herein over-express, or hyper-express, CT-B in comparison to the parental strain from which the vaccine candidate of the present invention is made or, alternatively, in comparison to a pathogenic wild type *V. cholera.* As described herein, such hyper-expression is important for eliciting production of anti-CT-B antibodies that also recognize LT, which antibodies furthermore are not only cross-reactive with LT, but neutralize LT function. The strains disclosed herein are able to express high levels of immunogenic CT-B polypeptides, e.g., at levels that exceed by at least 10-fold, at least 25-fold, at least 35-fold, at least 50-fold, or more the CT-B production of the parental strain of *Vibrio cholerae* from which the attenuated transformant *Vibrio cholerae* of the invention are prepared or of a wildtype pathogenic *V. cholerae.* For example, as shown in the examples to follow, the Peru-15(pCTB) embodiment of the present invention, in comparison to the Peru-15 parental strain, produces about 30-60-fold more CT-B antigen. Relative levels of CT-B expression can be measured by standard methods known in the art, e.g., antigen capture ELISA as described by Ryan et al., *Infect. Immun.,* 65(8):3118-25 (1997).

However, it is well known in the art that hyper-expression of recombinant polypeptides and, more particularly, recombinant expression of toxins, often proves to be toxic for the bacterial host cell. (See, Galen et al., *Trends Microbiol.*, 9(8): 372-6 (2001)). As previously noted, it is critical that the strains disclosed herein survive for a sufficient period to colonize the MALT, and produce and secrete the increased CT-B to elicit production of specific immunoglobulins.

Second, it is sometimes seen, when a bacterial host cell is used to overexpress a recombinant protein (e.g., a heterologous antigen), the survivability of the bacterial host cell may be adversely affected or the metabolic machinery of the host cell may be over-taxed by the recombinant expression system, which may in turn result in the transformed host cell being ineffective as an immunizing agent.

However, despite these known drawbacks, it has been discovered that the strains disclosed herein, while hyper-expressing CT-B in comparison to the parental strains, were surprisingly stable. This is particularly surprising in view of the belief that the increased toxin expression, that is, the hyper-expression of CT-B, might prove to be toxic for the strain. Moreover, the hyper-expressing CT-B strains retained the ability to elicit a vibriocidal immune response, that is, transforming the host *V. cholerae* did not take away the ability of the host to generate an anti-*V. cholerae* immune response.

The *V. cholerae* strains described herein and further set forth in the examples below, modified for increased expression of CT-B, elicit strong antibody responses in vivo in mammalian subjects, leading to high vibriocidal antibody titers as well as surprisingly high LT toxin neutralization titers. Data from two in vivo animal models indicates that the strains provide an immunogenic composition eliciting the desired dual antibody response for combating *V. cholerae* and ETEC(LT) infections.

In order to more fully illustrate the invention, the following non-limiting examples are provided.

EXAMPLES

Example 1

Bacterial Stains and Growth Media

Peru-15 is an attenuated O1 El Tor Inaba *Vibrio cholerae* strain that has been previously described (see, e.g., WO 95/18633). Peru-15 ΔglnA is a g/nA-deleted derivative of Peru-15. *Escherichia coli* strains TOP10 (Invitrogen, Carlsbad, Calif.) and MGN7027, a ΔglnA derivative of JM105 (Yanisch-Perron C. et al., *Gene,* 33(1):103-19 (1985)) were used for cloning. Luria-Bertani medium (LB) was obtained from Difco Laboratories Incorporated (Difco, Detroit Mich.). LB-V, a vegetable-based rich media, contained 20 g of HIVEG Luria Broth (HiMedia Laboratories, PVT. LTD., Mumbai, India) and 5 g NaCl per liter. For maintenance of GlnA balanced-lethal plasmids, cells were grown in M9V, which contained M9 minimal salts (Difco, Detroit Mich.), 2 mM $MgSO_4$, 0.5% glucose and 5 g HIVEG Acid Hydrolysate, a plant derived medium, (HiMedia Laboratories, PVT. LTD., Mumbai, India) per liter. For solid media, agar was added to 1.6%. Bacteria used to inoculate animals were grown in M9V at 37° C. to an $OD_{600}$ of 1.0, concentrated to the desired dose in PBS and administered the same day.

Construction of Peru-15 ΔglnA Balanced-Lethal Host Strain

Peru-15 ΔglnA was constructed by homologous recombination, essentially as described in Ryan et al., 2000, supra. Homologous recombination requires a functional recA gene, which has been deleted in Peru-15. Therefore, a plasmid carrying a functional copy of recA and a tetracycline resistance gene as a selectable marker, pLAFR-recA, was introduced into Peru-15 to yield Peru-15(pLAFR-recA).

Suicide plasmid pKEK70 carries a copy of glnA derived by PCR from *V. cholerae* classical Ogawa strain O395, with an internal 354-bp deletion eliminating amino acids 134 to 251 (Ryan et al., 2000, supra). In addition, it encodes bla, a gene for ampicillin resistance and sacB, which confers sensitivity to sucrose. Plasmid pKEK70 was introduced into Peru-15 (pLAFR-recA) by conjugation with selection for ampicillin resistance. Recombinants were grown in the absence of ampicillin and plated onto LB plates containing 10% sucrose. A sucrose-resistant, ampicillin-sensitive colony that required glutamine for growth was chosen. To cure the pLAFR-recA plasmid, the isolate was grown on antibiotic medium #3 supplemented with glutamine. Cells were scraped from the plate, suspended in PBS, plated onto LB plates and grown overnight at 37° C. Colonies were replica plated onto LB containing tetracycline to identify colonies that were tetracycline sensitive, indicating loss of the plasmid. A tetracycline sensitive colony was identified and confirmed to be recA negative by sensitivity to UV light. Loss of the plasmid was also confirmed by DNA miniprep analysis. This plasmid-free, ampicillin sensitive, tetracycline sensitive isolate was designated Peru-15 ΔglnA. The ΔglnA deletion was confirmed by PCR using primers that hybridize outside of the deleted sequences.

Construction of Plasmid pMEG-2350 and Peru-15pCTB

The ctxB gene was cloned by PCR with primers CT1146-PacI (CGACTTAATTAACCCGGCTTCATCGATCAGT AATACTTGCG) (SEQ ID NO: 1) and CT1664-BamHI (GACGGATCCCTTAATTTGCCATACTAATTGCG) (SEQ ID NO: 2) using chromosomal DNA prepared from *Vibrio cholerae* strain C6709 as the DNA template. The PCR product was cloned into plasmid pCR-Blunt-TOPO (Invitrogen, Carlsbad, Calif.) following the manufacturer's recommendations and electroporated into *E. coli* TOP10 cells. DNA sequence analysis confirmed that a selected clone had the expected sequence. The ctxB gene was subcloned as a 537 by EcoRI-BamHI fragment into plasmid pMEG-2106, a low-copy-number GlnA+ balanced lethal expression vector, yielding plasmid pMEG-2350 (FIG. 1). Features of plasmid pMEG-2350 include the glnA gene under the control of the $P_{cat}$ promoter, a pSC101 origin of replication and par locus, and the ctxB gene under the control of the $P_{trc}$ promoter.

Plasmid pMEG-2350 was introduced into Peru-15 ΔglnA by electroporation with selection for growth on glutamine-deficient M9V agar. The presence of the plasmid was verified by preparing plasmid DNA from overnight cultures using a QIAprep miniprep spin kit (QIAGEN, Hilden, Germany) and evaluating the DNA by agarose gel electrophoresis. One isolate was chosen and designated Peru-15(pCTB).

SDS-PAGE, Western Blots of Cell Supernates, Colony Blots and Quantitative ELISA

Cultures were grown in M9V broth to an optical density at 600 nm ($OD_{600}$) of 1.0. Cells were removed by centrifugation. The supernates were centrifuged again to remove any residual cells. Proteins in the supernates were concentrated 60-fold by precipitation with trichloroacetic acid (TCA). TCA pellets were suspended in loading dye and 10 μl were loaded on 15% SDS-PAGE gels, electrophoresed and subsequently stained with GelCode Blue Stain (Pierce). For evaluating pentamerization, cell free supernates were concentrated 70-fold with a Pierce iCON concentrator. For Western blot, duplicate gels were transferred to nitrocellulose. Blots were blocked overnight in PBS containing 0.1% TWEEN 20 and 5% milk. A polyclonal rabbit anti-CT-B antibody (Accurate Chemical and Scientific Corporation, Westbury, N.Y.) was added in PBS with 5% milk and incubated for two hours at room temperature. The filter was washed with PBS-TWEEN and the secondary HRP-conjugated anti-rabbit antibody (KPL) was added. Specific bands were detected using ECL detection reagents (Amersham Corporation, Louisville, Colo.).

The amount of CT-B secreted into culture supernates was determined by antigen capture ELISA as described by Ryan et al., 1997, supra.

Figure 2:
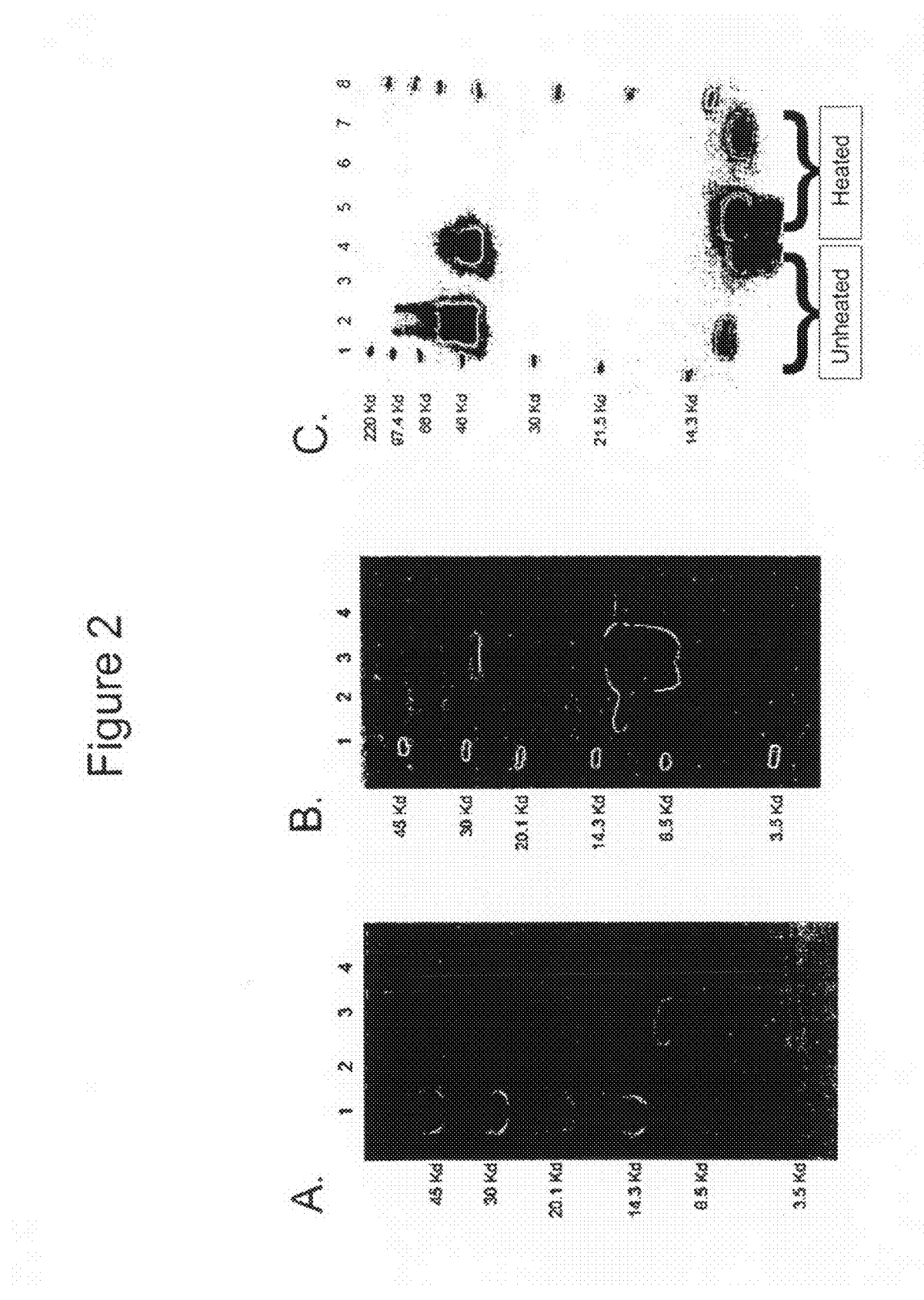
FIG. 2 is shows CT-B expression by Peru-15 and Peru-15 (pCTB). Cultures were grown to an $OD_{600}$ of 1.0 in M9-V broth. Supernates were concentrated and electrophoresed on 15% SDS acrylaminde gels.

CT-B expression was verified by evaluating TCA-precipitated culture supernates on stained COOMASSIE BLUE stained gels (FIG. 2A) and by Western blot (FIG. 2B). No CT-B was detected in cell pellets. Pentamerization of secreted CT-B was confirmed by electrophoresing supernate samples with and without heating (FIG. 2C). Unheated samples ran as a large complex that was disrupted by heating as expected for pentameric CT-B. A quantitative ELISA was employed to measure the amount of CT-B in the supernates from mid-exponential cultures of Peru-15(pCTB) and Peru-15. The results are expressed as CT-B/$OD_{600}$/ml to adjust for differences in optical density. Peru-15, which carries a single, chromosomal copy of ctxB, secreted 0.16 µg/ml, while Peru-15 (pCTB) surprisingly secreted 4.9 µg/ml CT-B. This difference represents a greater than 30-fold increase in CT-B expression and secretion. On a per cell basis, Peru-15(pCTB) produces 6.8 µg/$1 \times 10^9$ cells, compared to 0.17 µg/$1 \times 10^9$ cells produced by Peru-15.

Growth of Peru-15(pCTB) for Stability Experiments

In initial stability tests, a tube of frozen stock was thawed slightly and 5 µl transferred to 2 ml of M9V broth in a culture tube and grown for six hours with aeration at 37° C. Five µl was transferred to 50 ml of fresh M9V medium in a 250 ml flask and cells were grown with aeration for 20-24 hours. Five µl of cells were transferred to 50 ml of fresh medium. After a third cycle of transfer (40 generations), the culture was plated onto M9V agar and incubated overnight. Ten colonies were picked at random and streaked onto M9V plates. Overnight cultures of each of the ten isolates were grown in M9V broth. CT-B expression was determined by Western blot of TCA-precipitated supernates.

For the simulated manufacturing conditions stability test, all growth was performed with M9V media at 37° C. in triplicate. The frozen stock was streaked onto an M9V plate and incubated overnight. A single colony was used to inoculate 8 ml of broth in a 50 ml conical tube. Tubes were incubated overnight and 0.25 ml used to inoculate 25 ml of broth in a 250 ml flask. Flasks were vigorously aerated until the culture reached an $OD_{600}$ of 1.0. Glycerol was added to 15%, aliquots of 1 ml transferred to cryovials and stored at −80° C. overnight.

The next day, two vials were thawed and 1.6 ml were used to inoculate 50 ml of fresh broth in a 250 ml flask. Cultures were grown statically overnight and used to inoculate 300 ml of broth in a one-liter flask at a dilution of 1 to 20. Cultures were aerated and grown to an $OD_{600}$ of 1.0. Glycerol was added to 15% and 1 ml aliquots were frozen at −80° C. This process was repeated once more.

The final vials, representing 25 generations of growth, were thawed and plated onto agar plates. Ninety-eight colonies from each of the three triplicate runs were patched onto M9V plates and incubated overnight. Peru-15 was also included as a control. CT-B expression was evaluated by colony blot using the same antibodies as those described above for Western blot. CT-B-expressing colonies were detected using ECL detection reagents (Amersham Corporation, Louisville, Colo.).

Aerated cultures were grown for ~40 generations and plated as described above. Ten colonies were picked at random, grown overnight and evaluated by western blot for secreted CT-B. All ten colonies expressed levels of CT-B indistinguishable from the starting culture.

Figure 3:
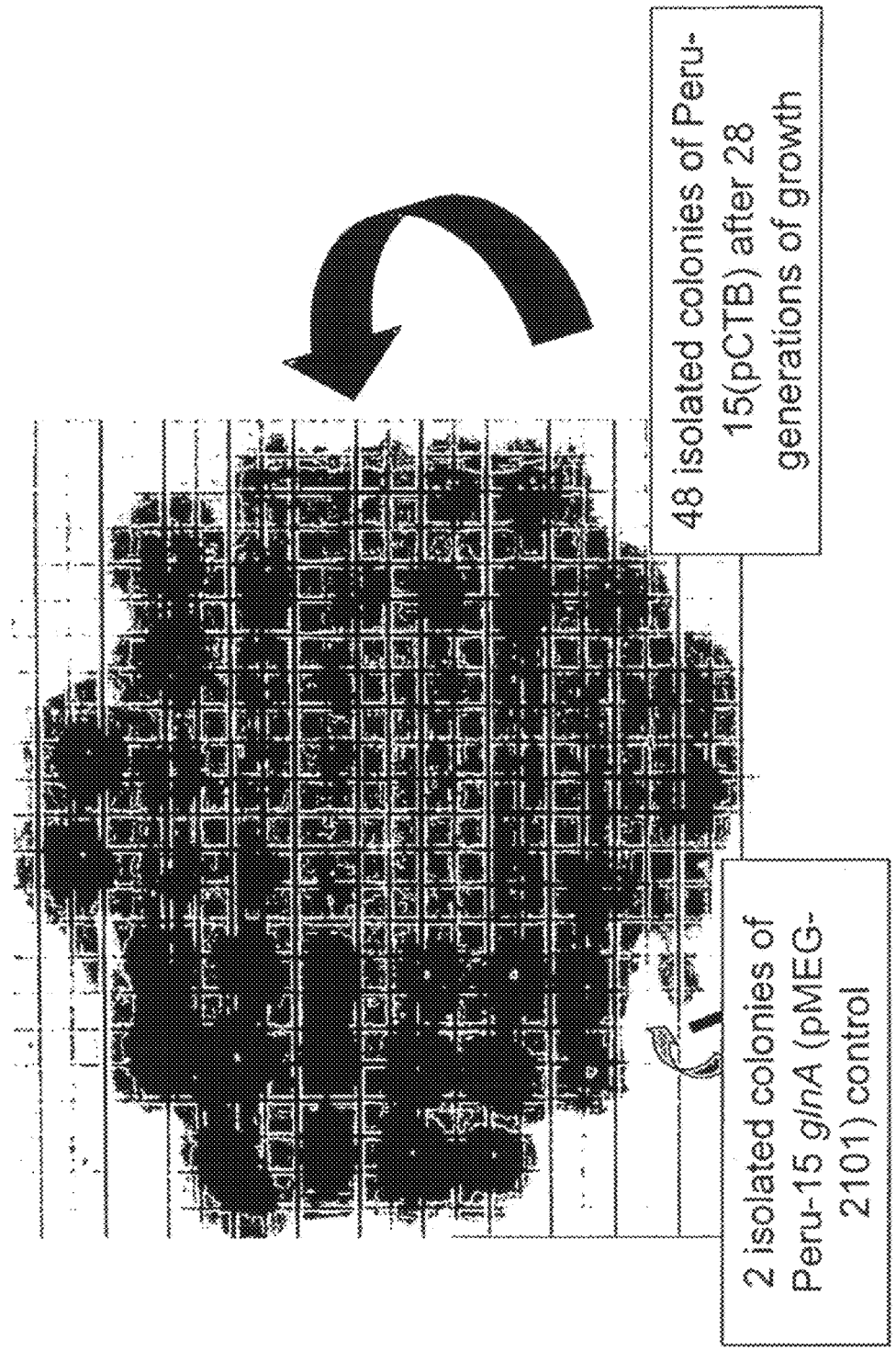
FIG. 3 is a colony blot of Peru-15(pCTB) isolates after 28 generations of growth. Peru-15 control and Peru-15(pCTB) strains were grown under conditions designed to mimic manufacturing conditions. Colonies were patched onto M9-V plates and probed with anti-CT-B antibody.

In a second experiment run in triplicate as described above, cells were grown in M9V for a total of ~28 generations under conditions designed to simulate the manufacturing processes used to create cGMP Seed Bank and Final Drug Product. The final culture was plated and a colony blot assay was performed. 100% (294 of 294) of the colonies tested retained expression levels indistinguishable from the Peru-15(pCTB) starting culture and were easily distinguishable from the low level expression exhibited by Peru-15 (see, FIG. 3). These data indicate that CT-B expression was surprisingly stable under the rigorous conditions used for the manufacture of Peru-15(pCTB), particularly in view of the 30-fold increase in CT-B expression compared to the parent strain. This is the first example of such expression in Vibrio. This stability is surprising because it was believed that the increased toxin expression, that is, the hyper-expression of CT-B, might prove to be toxic for the strain (Galen et al., *Trends Microbiol.*, 9(8):372-6 (2001)); however, as shown in this example, the strain remains stable and continues to hyper-express CT-B after at least 28 generations.

Immunogenicity of Peru-15(pCTB) and Peru-15 in Intranasally Immunized Mice

Groups of five BALB/c mice (Charles River, Wilmington, Mass.) were immunized intranasally with $1 \times 10^9$ CFU of the test organism in 20 µl of PBS on Day 0 and boosted on Day 28. Serum samples were taken on days 21 and 42 by tail bleed. A final serum sample was collected on day 56 by cardiac puncture when the mice were terminated. Serum IgG was analyzed by enzyme-linked immunosorbent assay (ELISA). 96-well polystyrene plates were coated with 100 ng/well of purified CT-B (Sigma-Aldrich, Saint Louis, Mo.) overnight at 4° C. Wells were blocked with 2% casein Tris-HCl pH 7.6 for 30 minutes at room temperature. Endpoint titers were determined by 2-fold serial dilutions of a one hundred-fold initial dilution in casein Tris-HCl, pH7.6. Serum dilutions were incubated on the plate for 2 hours at room temperature. The wells were washed, followed by the addition of a goat anti-mouse IgG alkaline phosphate-conjugated antibody (KPL, Gaithersburg, Md.) for 1 hour at room temperature. The assay was developed by the addition of BluePhos Microwell Substrate (KPL Gaithersburg, Md.) and read after 10 minutes at room temperature at a wavelength of 630 nm.

Mice inoculated with Peru-15(pCTB) developed high anti-CT-B titers, with geometric mean titers (GMT) of 3,200 by day 42 (see, Table 1). The anti-CT-B titers for all mice inoculated with Peru-15 were less than 100 at all time points tested; a 32-fold minimum difference in serum IgG responses between the two vaccine strains was observed. This experiment was repeated twice with similar results (GMT≧3,200 for Peru-15(pCTB) by day 56 and GMT<100 for Peru-15). These data strongly demonstrate that increasing the amount of secreted recombinant CT-B leads to a proportional increase in anti-CT-B antibody immune response. This observation was again somewhat surprising because the antigen to antibody relationship is not linear, that is, the amount of antibody produced tends to plateau after a certain level of exposure to the antigen. Increasing the amount of antigen does not always lead to increased immune response; however, as shown herein, a 30-fold increase in CT-B expression in Peru-15pCTB led to an almost equal 32-fold difference in serum IgG.

TABLE 1

Geometric mean serum IgG titers against CT-B from mice immunized with Peru-15 or Peru-15(pCTB)

| Day | Peru-15 Titer | Peru-15pCTB titer (range) |
|-----|---------------|---------------------------|
| 0   | <100          | <100                      |
| 21  | <100          | 172 (100-800)             |
| 42  | <100          | 3200 (1600-6400)          |
| 56  | <100          | 3200 (1600-12800)         |

Immunogenicity of Peru-15(pCTB) and Peru-15 in Orally Immunized Rabbits

The oral rabbit model has proven useful for evaluating the immunogenicity of Peru-15 prior to human studies (Linnetz et al., *Contemporary Topics*, 43(4):58 (2004)). Two experiments were performed in which rabbits were administered a single orogastric dose of either Peru-15 or Peru-15(pCTB).

New Zealand White rabbits (Milbrook Breeding Labs, Amherst, Mass.) were deprived of food and water overnight prior to immunization. At time zero, (t=0) anesthesia was administered intramuscularly with a cocktail consisting of 50 mg/kg ketamine and 3 mg/kg xylazine. At t=20 minutes, cimetidine (50 mg/kg) was administered via intravenous injection. Cimetidine was diluted to a 5 ml administered volume using sterile saline. At t=35 minutes, each rabbit was given 10 ml 0.5M $NaHCO_3$ (pH 8) via oral gavage using a disposable plastic animal feeding tube (Tyco Healthcare, Kendall Company #155722, Feeding Tube, 8fr×15", Sterile). At t=50 minutes, another 10 ml bicarbonate buffer was given immediately followed by a 10 ml dose of freshly grown bacteria in bicarbonate buffer. At t=80 minutes, intraperitoneal morphine (5 mg/kg) was administered, diluted to a 5 ml administered volume in sterile saline.

Assay for Detection of Rabbit Antibodies Specific for CT-B and LT

Serum antibodies were measured in an ELISA as follows. The wells of a 96-well microtiter plate (Nunc, Rochester, N.Y.) were coated with gangliosides ($GM_1$) at 100 ng/well in sodium carbonate coating buffer overnight at 4° C. Following incubation, $GM_1$ was decanted and the plates were coated with either CT-B or LT (List Biological Laboratories, Inc., Campbell, Calif.) in the same manner. Plates were then blocked at room temperature with a casein assay buffer in a TBS diluent. Rabbit sera were serially diluted in the assay buffer from 1:100 to 1:204,800; 100 µL of diluted sera were added per well and the plates were incubated for 2 hours at room temperature. A positive control was also added to each plate to ensure assay validity. In between all additions, plates were washed with TBS containing 0.1% TWEEN 20. An HRP goat anti-rabbit IgG (KPL, Inc., Gaithersburg, Md.) was added for 1 hour at room temperature followed by TMB Peroxidase Substrate (KPL, Inc., Gaithersburg, Md.) for 10 minutes at room temperature to develop the assay. The reaction was stopped with $H_2SO_4$ after which the plates were read at 450 nm on a Versamax microplate reader (Molecular Devices, Sunnyvale, Calif.). The antibody titer was determined as the inverse of the greatest dilution that yielded an absorbance at 450 nm that was two times over that of the background.

Serum anti-CT-B IgA antibodies were measured in an ELISA using a similar procedure using a specific IgA second antibody reagent.

Figure 4:
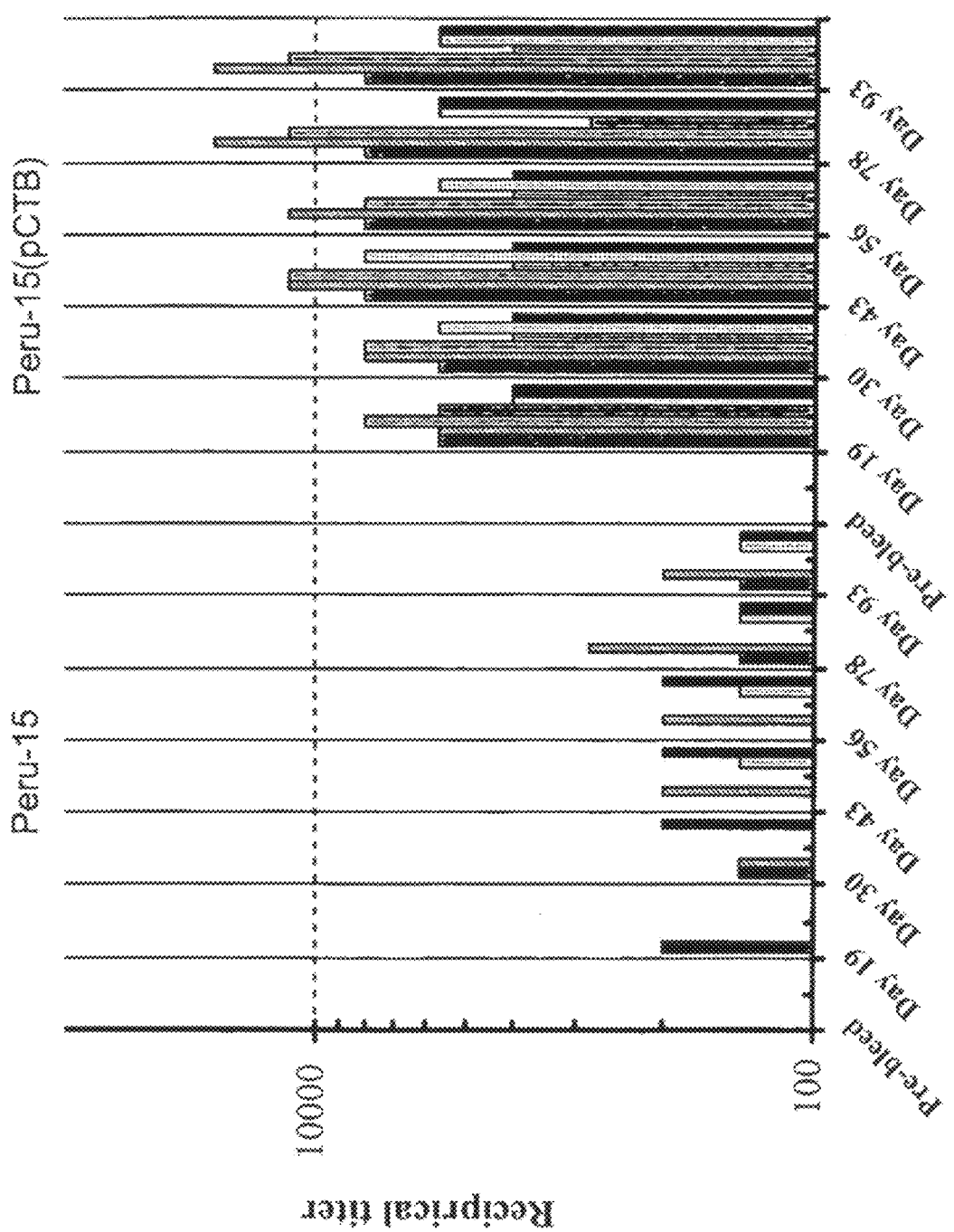
FIG. 4 is a chart showing anti-CT-B serum IgG titers in rabbits orally inoculated with either a single dose of Peru-15 or a single dose of Peru-15(pCTB).
Figure 5:
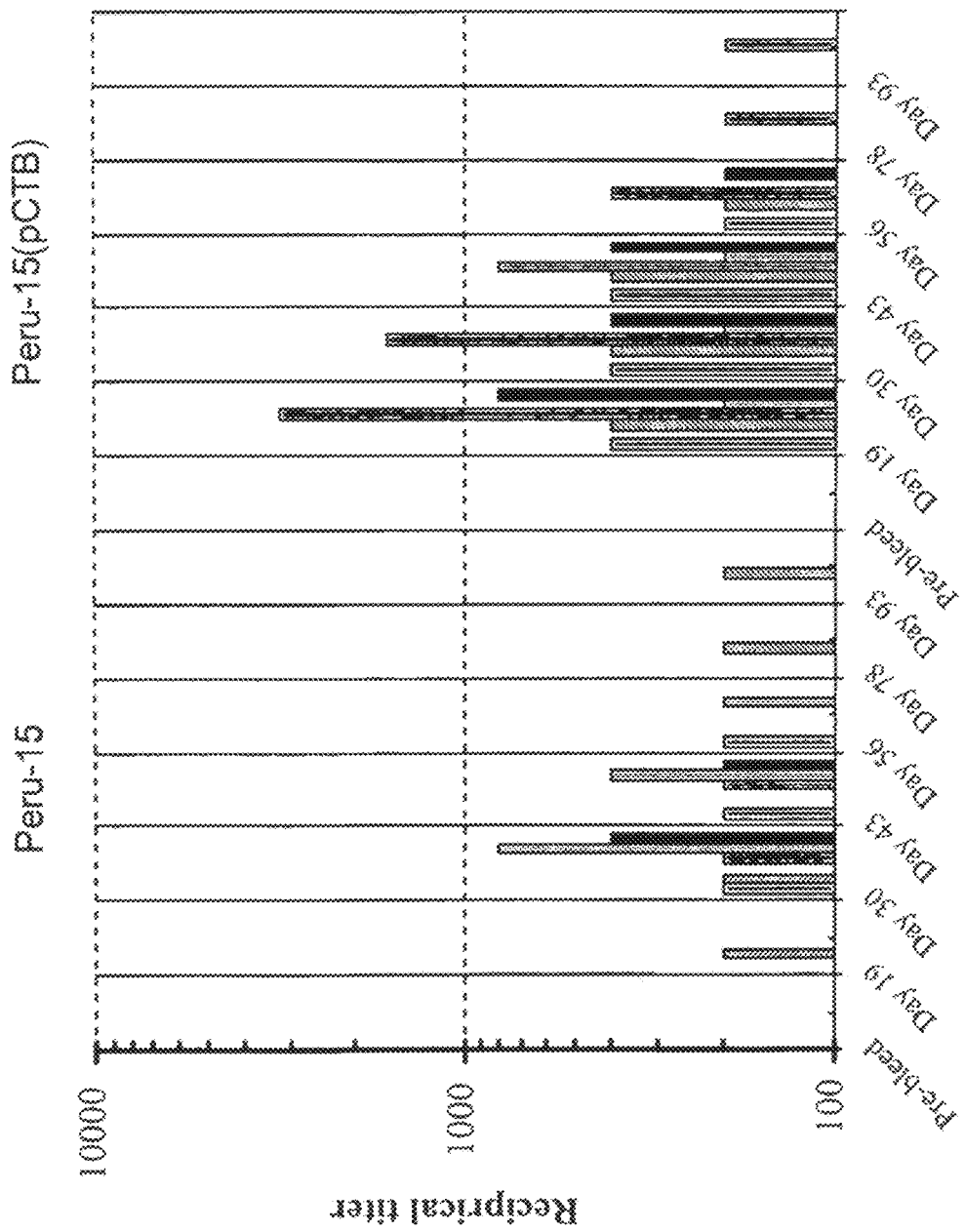
FIG. 5 is a chart showing anti-CT-B serum IgA geometric mean titers in rabbits orally inoculated with a single dose of Peru-15 or Peru-15(pCTB).

In both experiments, high serum IgG titers to CT-B were observed in animals inoculated with Peru-15(pCTB) (see, FIG. 4) by day 19, ~30-fold higher than animals inoculated with Peru-15. Peak GMT for Peru-15(pCTB) were >5000 on day 43, while the peak GMT for Peru-15 was 141. The serum IgG titers remained high through day 93, when the experiment was terminated. Coincidentally, the serum IgA titers also peaked on day 19 for animals inoculated with Peru-15 (pCTB) (see, FIG. 5) and remained high through day 43. Peru-15 induced slightly lower IgA titers, which peaked on day 30, but otherwise followed a similar time course.

Figure 6:
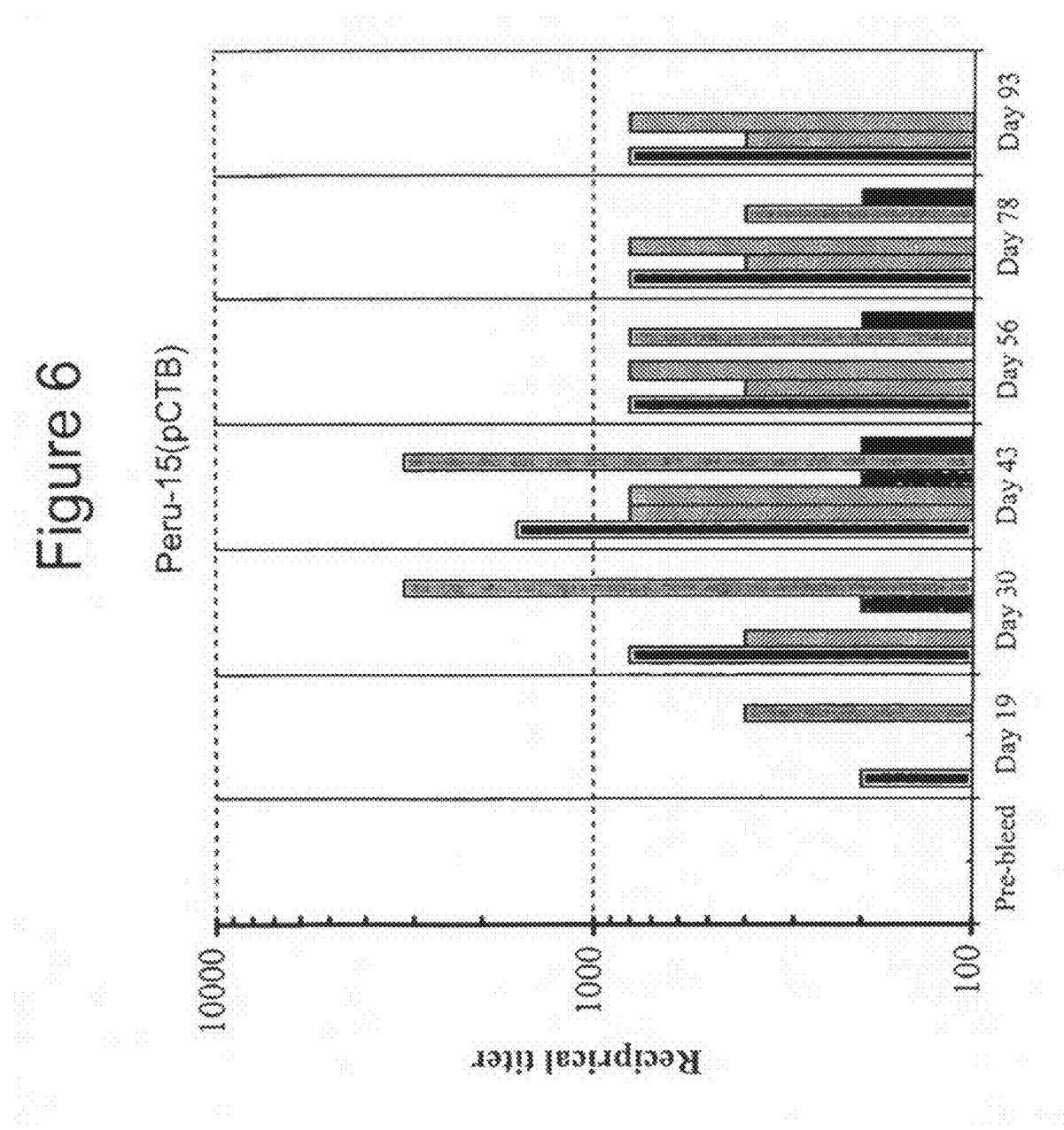
FIG. 6 is a chart showing anti-LT serum IgG geometric mean titers in rabbits orally inoculated with a single dose of Peru-15(pCTB). Anti-LT titers for all rabbits inoculated with Peru-15 were less than 50 (not shown).

Serum titers against LT holotoxin were also measured (see, FIG. 6). Unexpectedly, titers elicited in animals inoculated with Peru-15 were less than 50, except on day 43, when the titer was 56. In contrast, anti-LT titers in animals immunized with Peru-15(pCTB) reached a peak GMT of 713 on day 43, after which the titer slowly declined.

Vibriocidal Antibody Assay

Serum vibriocidal antibody titers were measured in a microassay. The endogenous complement activity of test sera was inactivated by heating sera at 56° C. for one hour. Fifty microliter serial two-fold dilutions of test sera and PBS were placed in wells of sterile 96-well tissue culture plates. Fifty microliters of a $10^8$ CFU/ml culture of *V. cholerae* N16961 in PBS with 22% guinea pig complement was added to each serum dilution, and plates were incubated at 37° C. for 1 hour. Then 150 µl of brain heart infusion broth was added to each well, and plates were incubated at 37° C. for 2.5 hours. The $OD_{600}$ was then measured. The titer was expressed as the reciprocal of the highest dilution yielding "no growth" in the well.

Figure 7:
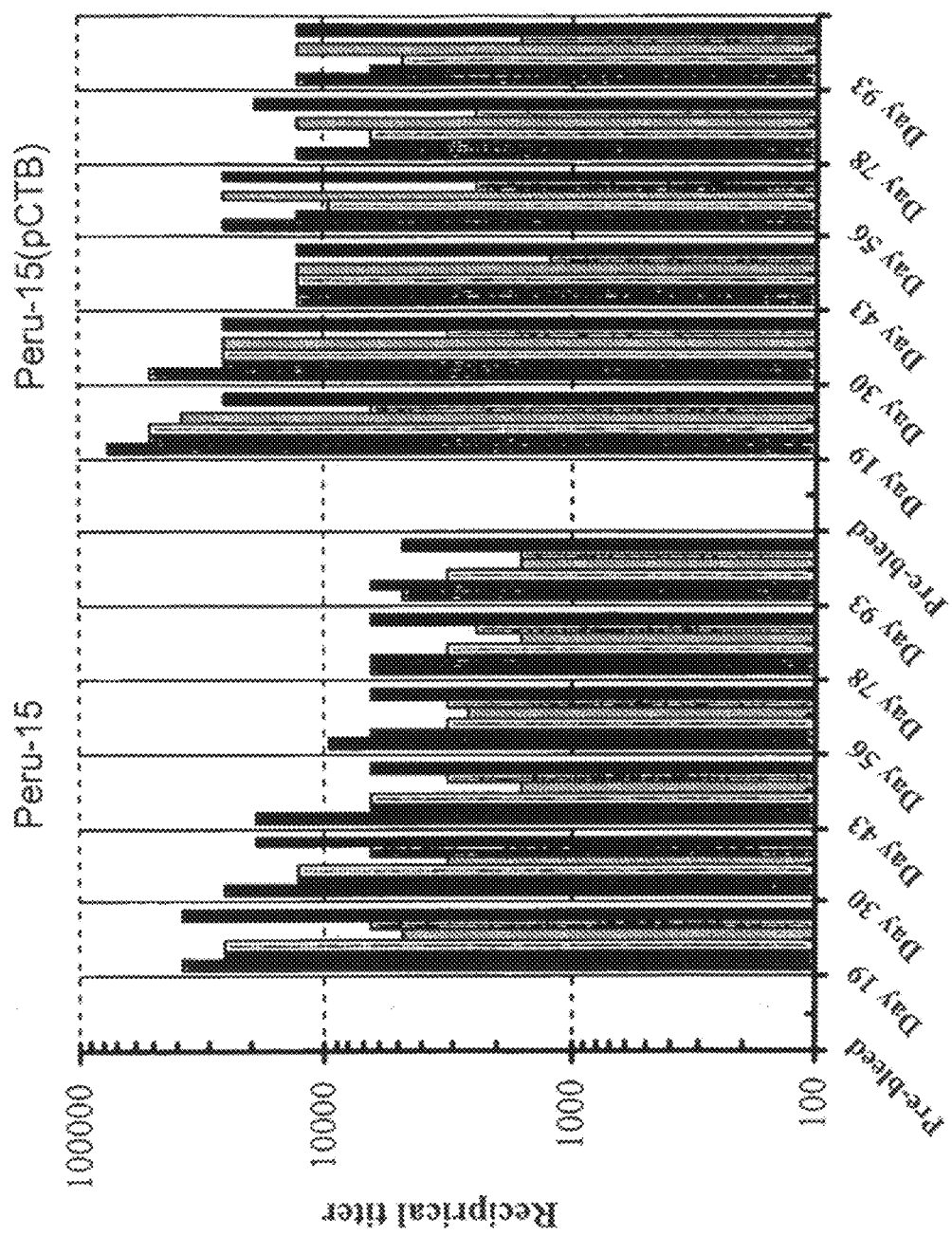
FIG. 7 is a chart showing vibriocidal titers in rabbits orally inoculated with a single dose of Peru-15 or Peru-15(pCTB).

The vibriocidal antibody GMTs for Peru-15(pCTB)-vaccinated rabbits were roughly twice that of those vaccinated with Peru-15 (see, FIG. 7). The kinetics of the elicited immune response were similar for Peru-15 and Peru-15 (pCTB), peaking at day 19 and gradually waning throughout the course of the experiment.

Heat-Labile Toxin (LT) Neutralization Assay

The capacity of sera from groups of mice immunized with either Peru-15 or Peru-15(pCTB) to neutralize the effect of LT holotoxin in a tissue culture model was also evaluated. The capacity of sera from immunized animals to neutralize the activity of LT was measured in a toxin neutralization assay using Y1 adrenal cells performed as described in Tauschek et al., *Proc. Natl Acad. Sci. USA*, 99(10):7066-7 (2002). Briefly, 250 pg of LT in DMEM was added to wells with a range of serum dilutions beginning at 1:40 into DMEM and incubated for one hour at 37° C. The mixture was added to wells containing $2 \times 10^4$ Y1 cells, incubated overnight, and the number of rounded cells per well was determined by visual examination.

Pooled pre-bleed samples from mice in both groups contained no detectable functional, or neutralizing antibody. However, the reciprocal GMT of sera from mice inoculated with Peru-15(pCTB) for the three experiments ranged from 1158 to 2660 (see, Table 2). These data support previous observations that anti-CT-B antibodies cross-react with LT and indicate that the immune response elicited by Peru-15 (pCTB) produces functional LT toxin-neutralizing antibody. Interestingly, neutralizing antibody GMTs from mice inoculated with Peru-15 ranged from 83-110, which was surprising, since we did not detect any anti-CT-B by ELISA.

When we examined day 56 sera from the rabbit experiments for the ability to neutralize LT, we found that animals vaccinated with Peru-15 had GMTs of 252 and 272 in the two experiments. Vaccination with Peru-15(pCTB) led to GMTs of 6400 and 6912, roughly a 25-fold increase. This correlates with the increase observed in anti-CT-B ELISA titers at that same time point (see, FIG. 4).

TABLE 2

Geometric mean LT toxin neutralization serum titers from animals inoculated with Peru-15 of Peru-15(pCTB)

| Experiment | Peru-15 | Peru-15(pCTB) | Fold increase |
|---|---|---|---|
| Mouse | | | |
| Experiment 1 | 110 | 1213 | 11 |
| Experiment 2 | * | 1158 | N/A |
| Experiment 3 | 83 | 2660 | 32 |
| Rabbit | | | |
| Experiment 1 | 272 | 6400 | 24 |
| Experiment 2 | 252 | 6912 | 27 |

* Peru-15 was not included in this experiment

The results above demonstrate that the live attenuated cholera/ETEC vaccine candidate, Peru-15(pCTB), genetically engineered to stably express CT-B at high levels, induces substantially higher titer CT-B and LT-specific antibodies than its parental strain Peru-15 in two distinct animal models. In murine immunogenicity experiments, two doses of Peru-15(pCTB) administered intranasally resulted in high serum titers, while the titers using Peru-15 were below detectable limits. In rabbit immunogenicity studies, a single dose of Peru-15 elicited peak anti-CT-B titers between 100 and 200, while Peru-15(pCTB) immunization elicited titers 10-25-fold higher, thereby establishing a strong link between higher levels of antigen expression and increased immune responses.

The dual immunogenicity data obtained in the rabbit model is significant for development of a useful human vaccine, since the clinical administration is an oral, single-dose regimen. A peak 50-fold increase in mean serum IgG titers against CT-B (see, FIG. 4) and a peak 14-fold increase in mean titers against LT (see, FIG. 6) following vaccination of rabbits with Peru-15(pCTB) compared to either Peru-15 or pre-bleeds from vaccinated animals were obtained. This 14-fold increase in anti-LT titers is greater than the 3.3-fold increase in anti-LT titers seen in volunteers who received a single dose of an oral whole-cell cholera vaccine containing 1 mg CT-B (Glenn et al., *Infect. Immun.,* 75(5):2163-70 (2007)). These results indicate that the level of CT-B production by the disclosed dual immunogenic microbe is adequate to induce an immune response somewhat comparable to a 1 mg bolus dose of CT-B.

The anti-CT-B IgG titers were approximately 7-fold higher than the anti-LT IgG titers (see, FIGS. 4 and 6). One reason for the observed difference is that while CT-B and LT-B are very similar, they are not identical, and there may be antibodies that are specific only for CT-B. While this explanation undoubtedly accounts in part for the observed disparity, there may also be a significant contribution caused by structural differences between using the B subunit alone and holotoxin in the ELISA assay. This point of view is supported by the finding that when serum from rabbits hyper-immunized with purified LT were evaluated in these two assays, it was found that the titers against CT-B were eight fold higher than the titers against LT. Therefore, it is likely that the assays are not sensitive enough to detect CT-specific antibodies; however the fact that the anti-CT-B antibodies generated in the experimental animals behave in a manner similar to antibodies generated against LT holotoxin is encouraging.

The vibriocidal titers observed in rabbits indicate that expression of high CT-B levels in Peru-15 has not diminished Peru-15(pCTB)'s potency as an immunogenic composition for eliciting protection against cholera. In fact, the vibriocidal titers were nearly two-fold higher at each time point, although the difference was not statistically significant ($p>0.05$) until day 57 ($p=0.02$).

As previously noted, over-expression of protective antigens derived from plasmids in live vectors can be detrimental to the host (Galen et al., 2001, supra). Several factors can increase the metabolic burden and thus the fitness and stability of a live bacterial vaccine expressing an antigen, including plasmid size, plasmid copy number, codon usage, and the expression system (Galen et al., 2001, supra). As a result, point mutations or deletions causing diminished gene expression can accumulate, resulting in a population of cells that lose the capacity to express immunogenic amounts of antigen. The expression of Peru-15(pCTB) after 40 generations of growth under laboratory conditions and after 28 generations of growth under simulated cGMP Seed Bank and final drug product manufacturing conditions was evaluated herein. In both cases, surprisingly no isolates lost the ability to secrete high levels of CT-B, indicating that Peru-15(pCTB) is appropriately stable for manufacture and clinical development.

In a previous study, college students given Dukoral® killed, whole-cell cholera vaccine developed anti-CT-B reciprocal geometric mean titers of 152 by day 35 (Scerpella et al., *J. Travel Med.,* 2(1):22-27 (1995), a 12-fold increase above baseline. Volunteers receiving Peru-15 achieved a titer of 48 by day 21 of the study (Sack et al., *J. Infect. Dis.,* 176(1):201-5 (1997). If we extrapolate from our animal data, it is likely that vaccination with Peru-15(pCTB) will induce titers higher than the levels obtained with either Dukoral or Peru-15, leading to an improved dual immunogenic vaccine candidate. Moreover, CT-B seroconversion with Peru-15, CVD 103-HgR, or Dukoral® was not 100% (see, Scerpella et al., 1995; Sack et al., 1997; Cryz et al., *Vaccine,* 8(6):577-80 (1990)). This is consistent with the results disclosed herein for Peru-15 in both animal models (see, Table 1 and FIG. 4). None of the mice seroconverted and only 3 of 6 rabbits had seroconverted by day 56 (titer>100). In contrast, when inoculated with Peru-15(pCTB), surprisingly all of the mice had seroconverted by day 42 and all of the rabbits seroconverted by day 19, suggesting that the Peru-15(pCTB) dually immunogenic microbe will lead to both higher anti-CT-B IgG titers and a higher seroconversion rate among subjects.

These studies demonstrate the superiority of Peru-15 (pCTB) as a genetically engineered live attenuated *Vibrio cholerae* vaccine candidate with dual immunogenicity for providing protection against *V. cholerae* and enterotoxinogenic *E. coli* infection.

All patents, applications, and publications cited in the above text are incorporated herein by reference.

Other variations and embodiments of the invention described herein will be apparent to practitioners in this field in view of the foregoing disclosure. All such obvious variants of the specific embodiments described herein are within the scope of the invention described and defined in the claims to follow.

Microorganism Deposit

Under the terms of the Budapest Treaty on the International Recognition of the Deposit of Microorganisms for the Purpose of Patent Procedure (Dec. 2, 2004), one or more of the following strains of *V. cholerae* was deposited with the American Type Culture Collection ("ATCC®", 10801 University Blvd., Manassas, Va., 20110-2209 USA): *V. cholerae* strain Peru-15 (ATCC Accession No. 55635) (existing deposit) and *V. cholerae* strain Peru-15pCTB (ATCC Accession No. PTA-9130, deposited Apr. 8, 2008).

What is claimed is:

1. An immunogenic composition comprising *Vibrio cholerae* strain Peru-15 pCTB, having the ATCC designation PTA-9130.

2. A method of eliciting neutralizing anti-cholera toxin B (CT-B) antibodies cross-reactive with enterotoxigenic *Escherichia coli* (ETEC) heat labile toxin (LT) and vibriocidal antibodies in a mammalian subject comprising oral or intranasal administration to said subject an amount of the immunogenic composition of claim 1 sufficient to elicit said antibodies in said subject.

* * * * *

SEQUENCE LISTING

<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: PCR primer

<400> SEQUENCE: 1
cgacttaatt aacccggctt catcgatcag taatacttgc g        41

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
gacggatccc ttaatttgcc atactaattg cg        32